United States Patent
Chen et al.

(10) Patent No.: US 11,354,566 B1
(45) Date of Patent: Jun. 7, 2022

(54) CAUSAL INFERENCE AND POLICY OPTIMIZATION SYSTEM BASED ON DEEP LEARNING MODELS

(71) Applicant: SAS Institute Inc., Cary, NC (US)

(72) Inventors: Xilong Chen, Chapel Hill, NC (US); Douglas Allan Cairns, Durham, NC (US); Jan Chvosta, Raleigh, NC (US); David Bruce Elsheimer, Clayton, NC (US); Yang Zhao, Raleigh, NC (US); Ming-Chun Chang, Cary, NC (US); Gunce Eryuruk Walton, Raleigh, NC (US); Michael Thomas Lamm, Cary, NC (US)

(73) Assignee: SAS Institute Inc., Cary, NC (US)

( * ) Notice: Subject to any disclaimer, the term of this patent is extended or adjusted under 35 U.S.C. 154(b) by 0 days.

(21) Appl. No.: 17/507,376

(22) Filed: Oct. 21, 2021

Related U.S. Application Data

(60) Provisional application No. 63/186,067, filed on May 8, 2021, provisional application No. 63/168,231, filed (Continued)

(51) Int. Cl.
*G06N 3/04* (2006.01)
*G16H 50/50* (2018.01)
(Continued)

(52) U.S. Cl.
CPC .......... *G06N 3/0454* (2013.01); *G06N 3/002* (2013.01); *G06N 3/004* (2013.01); *G06N 5/04* (2013.01); *G16H 50/50* (2018.01); *G06N 5/045* (2013.01)

(58) Field of Classification Search
CPC ...... G06N 3/002; G06N 3/004; G06N 3/0454; G06N 5/04; G16H 50/50
See application file for complete search history.

(56) References Cited

PUBLICATIONS

Farajtabar, Mehrdad, et al. "Balance regularized neural network models for causal effect estimation." arXiv preprint arXiv:2011. 11199 (2020). (Year: 2020).*

(Continued)

*Primary Examiner* — Benjamin P Geib
(74) *Attorney, Agent, or Firm* — Bell & Manning, LLC

(57) ABSTRACT

A treatment model that is a first neural network is trained to optimize a treatment loss function based on a treatment variable t using a plurality of observation vectors by regressing t on $x^{(1)}$, z. The trained treatment model is executed to compute an estimated treatment variable value $\hat{t}_i$ for each observation vector. An outcome model that is a second neural network is trained to optimize an outcome loss function by regressing y on $x^{(2)}$ and an estimated treatment variable t. The trained outcome model is executed to compute an estimated first unknown function value $\hat{\alpha}(x_i^{(2)})$ and an estimated second unknown function value $\hat{\beta}(x_i^{(2)})$ for each observation vector. An influence function value is computed for a parameter of interest using $\hat{\alpha}(x_i^{(2)})$ and $\hat{\beta}(x_i^{(2)})$. A value is computed for the predefined parameter of interest using the computed influence function value.

30 Claims, 6 Drawing Sheets

Related U.S. Application Data on Mar. 30, 2021, provisional application No. 63/154,629, filed on Feb. 26, 2021, provisional application No. 63/152,756, filed on Feb. 23, 2021.

(51) Int. Cl.
*G06N 5/04* (2006.01)
*G06N 3/00* (2006.01)

(56) References Cited

PUBLICATIONS

Sharma, Ankit, et al. "Multimbnn: Matched and balanced causal inference with neural networks." arXiv preprint arXiv:2004.13446 (2020). (Year: 2020).*

Shi, Claudia, David M. Blei, and Victor Veitch. "Adapting Neural Networks for the Estimation of Treatment Effects." arXiv preprint arXiv:1906.02120 (2019). (Year: 2019).*

Farrell, M. H., T. Liang, S. Misra. (2019) Deep Neural Networks for Estimation and Inference. arXiv:1809.09953v3. Forthcoming in Econometrica.

Farrell, M. H., T. Liang, S. Misra. (2020) Deep Learning for Individual Heterogeneity. arXiv:2010.14694.

Athey et al., "Policy Learning with Observational Data," (2020) arXiv:1702.02896v6.

* cited by examiner

CAUSAL INFERENCE AND POLICY OPTIMIZATION SYSTEM BASED ON DEEP LEARNING MODELS

CROSS-REFERENCE TO RELATED APPLICATIONS

The present application claims the benefit of and priority under 35 U.S.C. § 119(e) to U.S. Provisional Patent Application No. 63/186,067 filed May 8, 2021, to U.S. Provisional Patent Application No. 63/168,231 filed Mar. 30, 2021, to U.S. Provisional Patent Application No. 63/154,629 filed Feb. 26, 2021, and to U.S. Provisional Patent Application No. 63/152,756 filed Feb. 23, 2021, the entire contents of which are hereby incorporated by reference.

BACKGROUND

Causal inference is an important and active field in both academia and industry. Causal inference identifies causes, measures their effects, and directs policy making. Since randomized controlled trials are often expensive or even impossible, the causal effect may be estimated from observational data. There are several technical difficulties to do so, especially in the big-data world. For example, there may be a large number of potential covariates; there may be unknown nonlinearity relationship between those covariates and an outcome variable and a treatment variable, and the variables may be discrete, continuous, or mixed.

Here, the outcome variables are a result of interest, and the treatment variables are a possible cause that describes the action, the intervention, or the treatment assignment. The other variables describe characteristics of the object of interest (such as a patient, customer, store, etc.) or the situation and context. The outcome variables or treatment variables may be a vector of variables, although in most real-world cases, they are scalars. The causal effect, also known as the treatment effect, is the effect of the treatment variables on the outcome variables.

For example, in the process of studying the effect of a new medicine on a patient, the outcome is the final health status of the patient, and the treatment is whether to assign the medicine to the patient. If the causal effect of any patient can be estimated, the policy making is to set the rule that determines the assignment of medicine or not based on the patient's characteristics that may be described by hundreds of variables.

Another example is in personalized pricing. The outcome variable is the demand, the treatment variable is the price, and the other covariates may include a time of year, a market status, and a customer's personal information and buying history. The causal effect between the demand and the price given the other variables is estimated first. The policy optimization may determine a best personalized price for any given customer (who may be a new customer) to maximize the revenue, which is often defined as a difference between the product of demand and price and the cost.

SUMMARY

In an example embodiment, a computer-readable medium is provided having stored thereon computer-readable instructions that when executed by a computing device, cause the computing device to train neural network models to estimate a value for a parameter of interest for causal inference. A treatment model is trained to optimize a treatment loss function based on a treatment variable t using a plurality of observation vectors. Covariate variable values for a plurality of covariate variables, a treatment variable value for the treatment variable t, an instrument variable value for an instrument variable z, and an outcome variable value for an outcome variable y are defined for each observation vector of the plurality of observation vectors. The treatment model is a first neural network that includes a first plurality of connected neural network layers and is trained to regress t on $x^{(1)}, z$, wherein $x_i^{(1)}$ indicates a first set of covariate variable values defined for a first set of covariate variables $x^{(1)}$ selected from the plurality of covariate variables, where i indicates an $i^{th}$ observation vector of the plurality of observation vectors. The trained treatment model is executed to compute an estimated treatment variable value $\hat{t}_i$ for each observation vector of the plurality of observation vectors. An outcome model is trained to optimize an outcome loss function. The outcome model is a second neural network that includes a second plurality of connected neural network layers and is trained to regress y on $x^{(2)}$ and an estimated treatment variable $\hat{t}$, wherein $x_i^{(2)}$ indicates a second set of covariate variable values defined for a second set of covariate variables $x^{(2)}$ selected from the plurality of covariate variables. The trained outcome model is executed to compute an estimated first unknown function value $\hat{\alpha}(x_i^{(2)})$ and an estimated second unknown function value $\hat{\beta}(x_i^{(2)})$ for each observation vector of the plurality of observation vectors. An influence function value is computed for a predefined parameter of interest using the estimated first unknown function value $\hat{\alpha}(x_i^{(2)})$ and the estimated second unknown function value $\hat{\beta}(x_i^{(2)})$ for each observation vector of the plurality of observation vectors. A value is computed for the predefined parameter of interest using the computed influence function value. The computed value for the predefined parameter of interest is output.

In another example embodiment, a computing device is provided. The computing device includes, but is not limited to, a processor and a computer-readable medium operably coupled to the processor. The computer-readable medium has instructions stored thereon that, when executed by the processor, cause the computing device to train neural network models to estimate a value for a parameter of interest for causal inference.

In yet another example embodiment, a method of training neural network models to estimate a value for a parameter of interest for causal inference is provided.

Other principal features of the disclosed subject matter will become apparent to those skilled in the art upon review of the following drawings, the detailed description, and the appended claims.

BRIEF DESCRIPTION OF THE DRAWINGS

Illustrative embodiments of the disclosed subject matter will hereafter be described referring to the accompanying drawings, wherein like numerals denote like elements.

DETAILED DESCRIPTION

Figure 1:
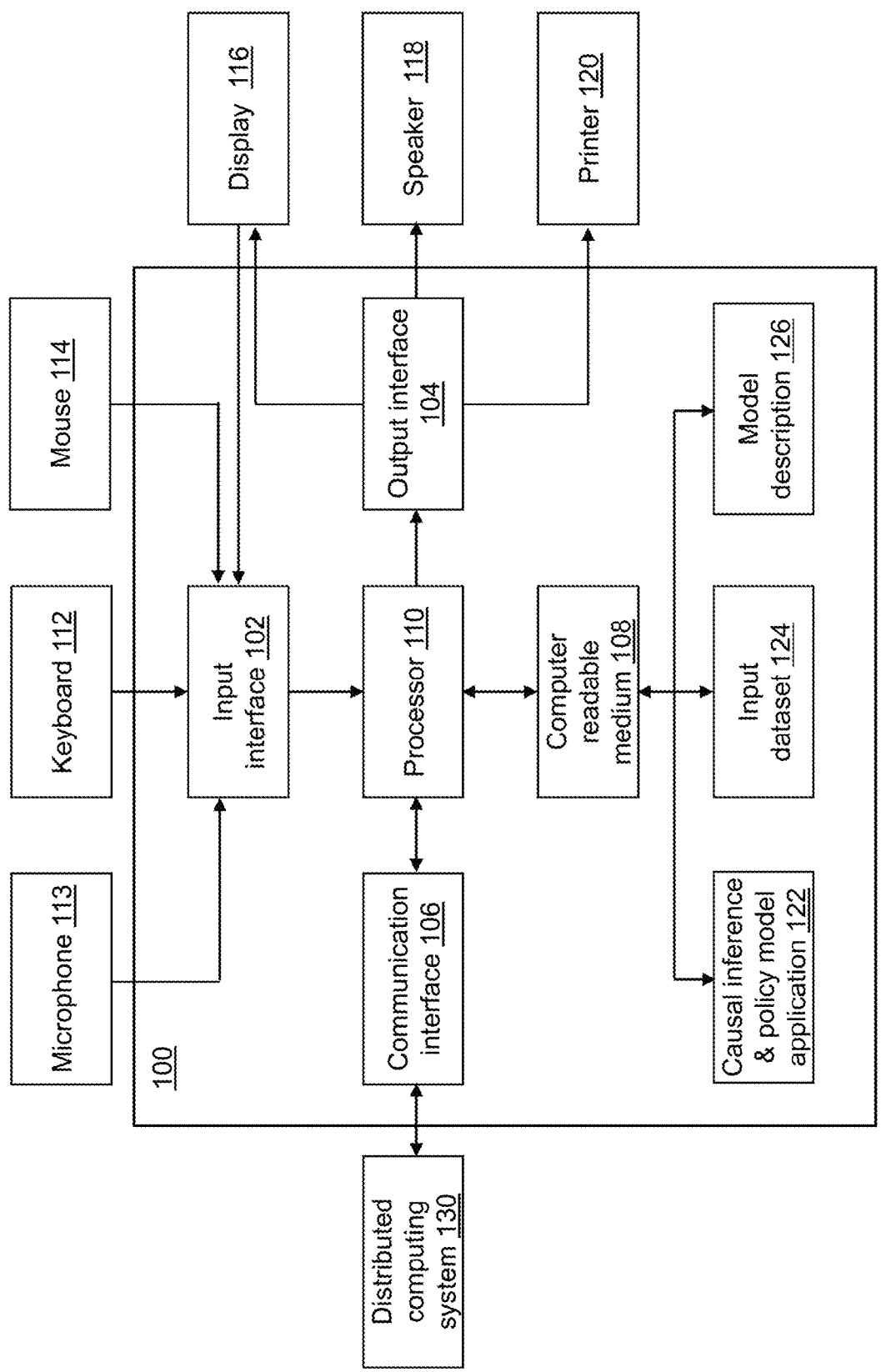
FIG. 1 depicts a block diagram of a model training device in accordance with an illustrative embodiment.

Neural networks are a class of machine learning models that consist of one or more transformation layers. Loosely speaking, each layer i has $d_i$ inputs, $h_i$ outputs, a set of weights denoted by the matrix $W_i \in \mathbb{R}^{h_i \times d_i}$, a set of inputs $m_i \in \mathbb{R}^{d_i}$ (neurons), and a bias term $\beta_i \in \mathbb{R}^{h_i}$. The corresponding output of the layer is itself a set of neurons $\alpha_i(m_i) \in \mathbb{R}^{h_i}$ defined by the transformation:

$$\alpha_i(m_i) = \sigma(W_i m_i + \beta_i),$$

where $\sigma$ denotes a corresponding activation function. If there are $l$ layers, the union of the set of parameters $\cup \{W_i, \beta_i\}_{i=1}^{l}$, becomes the corresponding optimization variables or parameters. For simplicity, a map from this set to a weight vector $w \in \mathbb{R}^d$ is assumed, where d corresponds to a total number of variables across all layers.

Deep learning models are a class of neural networks consisting of many layers. As in other machine learning approaches, in deep learning, an objective or loss function is minimized $$\min_{w \in \mathbb{R}^d} f(w) = \frac{1}{n} \sum_{i=1}^{n} f_i(w),$$

where each objective function $f_i(w)$ provides a measure of accuracy for the deep learning model applied to the $i^{th}$ observation in input dataset 124 which includes n observations or samples. For loss functions such as those arising in deep-learning models, $f(w)$ may be nonconvex while both d and n may be arbitrarily large.

Causal inference identifies the causes, measures their effects, and directs policy making. Deep Neural Networks (DNNs) can be applied to solve causal inference and policy optimization problems to train a treatment model and an outcome model to estimate unknown functions used to compute parameters of interest such as an average treatment effect (ATE) and to train a policy model to obtain an optimized policy to be applied to a new observation. For example, a treatment may be selected for a new patient using the optimized policy model or a personalized price may be selected for a new customer based on the optimized policy model. The treatment may indicate a drug regimen, a transfer to the intensive care unit, a test regimen, etc. As provided herein, a DNN estimates unknown functional forms with high-dimensional mixed-discrete-and-continuous covariates consistently with a convergence rate that is fast enough so that non-parametric estimates result in root-n-consistent estimators of parameters of interest. There are two stages: (1) construct appropriate DNNs and calculate the appropriate influence functions to estimate the parameters of interest for causal inference, and (2) exploit the estimates to construct a DNN for policy optimization.

There are two main models in the causal inference: 1) a treatment model and an outcome model. When the treatment is binary or discrete, the treatment model may be referred to as a propensity score model, which describes a treatment assigning probability conditioned on a first set of covariates, $x^{(1)}$, such that $$\text{Prob}\{T \in A | X = x^{(1)}\} p(x^{(1)})$$

where T is a treatment, A is an event (e.g., A is $\{1\}$, when T is binary), and X is the first set of covariates whose realized value is $x^{(1)}$. When the treatment is continuous, the treatment model may be a regression, such that $$E(T|X = x^{(1)}) = p(x^{(1)})$$

where $E(.|.)$ denotes a conditional expectation. When there are unobserved confounders and some instrumental variables z are available, a propensity score model may become $\text{Prob}\{T \in A | X = x^{(1)}, Z = z\} = p(x^{(1)}, z)$, and the regression model may become $E(T|X = x^{(1)}, Z = z) = p(x^{(1)}, z)$. In the treatment model, $p(.)$ or $p(.,.)$ is an unknown function to be estimated, which could be in any nonlinear form. The first set of covariates, $x^{(1)}$, may be referred to as the treatment model covariates.

The outcome model describes how an outcome depends on the treatment and a second set of covariates, $x^{(2)}$, where $x^{(2)}$ may be the same as or different from $x^{(1)}$. The second set of covariates, $x^{(2)}$, may be referred to as the outcome covariates. When the outcome is continuous, the outcome model may be defined as a regression $$E(Y|X = x^{(2)}, T = t) = G(\alpha(x^{(2)}) + \beta(x^{(2)})'t)$$

where Y is the outcome, t is the treatment in K×1 vector form, $E(Y|X = x^{(2)}, T = t)$ is a conditional expectation function of the outcome Y given the second set of covariates $x^{(2)}$ and the treatment t, $G(\alpha(x^{(2)}) + \beta(x^{(2)})'t)$ is a predefined function (e.g., $G(\alpha(x^{(2)}) + \beta(x^{(2)})'t) = \alpha(x^{(2)}) + \beta(x^{(2)})'t$, the identity function $G(u) = u$, where $u = \alpha(x^{(2)}) + \beta(x^{(2)})'t$), $\alpha(x^{(2)})$ and $\beta(x^{(2)})$ are unknown functions to be estimated, and ' indicates a transpose of a vector or matrix.

When the outcome is discrete, the outcome model may be defined in probability form. For example, when the outcome is binary, the outcome model is a logit model $$Pr(Y = 1 | X = x^{(2)}, T = t) = G(\alpha(x^{(2)}) + \beta(x^{(2)})'t)$$

where $G(u) = (1 + e^{-u})^{-1}$ is the logit function.

Deep learning may be applied to causal inference using a two-step semi-parametric framework, where the first step is a non-parametric step and a second step is a parametric step. In the first step of non-parametric estimation, a treatment DNN is trained to estimate the unknown function, $p(x^{(1)})$ or $p(x^{(1)}, z)$ and an outcome DNN is trained to estimate the unknown functions, $\alpha(x^{(2)})$, and $\beta(x^{(2)})$.

A matrix function $\Lambda(.)$ may be defined as $\Lambda(.) = E(\dot{G}(\alpha(x^{(2)}) + \beta(x^{(2)})'t)\tilde{t}\tilde{t}')$, where $E(.)$ is the conditional expectation function, $\dot{G}(\alpha(x^{(2)}) + \beta(x^{(2)})'t)$ is the gradient of $G(\alpha(x^{(2)}) + \beta(x^{(2)})'t)$, and $\tilde{t} = (1 t')'$. When $\dot{G}(\alpha(x^{(2)}) + \beta(x^{(2)})'t)$ is a constant c, and the treatment t is a binary scalar, $\Lambda(.)$ can be estimated using $p(x^{(1)})$ because $$E(\dot{G}(\alpha(x^{(2)}) + \beta(x^{(2)})'t)\tilde{t}\tilde{t}') = cE(\tilde{t}\tilde{t}') = cE\left(\begin{pmatrix} 1 & t \\ t & t^2 \end{pmatrix}\right) = c\begin{pmatrix} 1 & p(x^{(1)}) \\ p(x^{(1)}) & p(x^{(1)}) \end{pmatrix}.$$

Otherwise, each element of $\Lambda(.)$ is an unknown function that can be estimated using $K(K+1)/2$ DNNs referred to as the matrix DNNs, where K is a dimension of the treatment t that is a vector. For example, $\Lambda(.) = (\lambda_{ij}(.))_{i,j=1, \ldots, 1+K}$, where $\lambda_{ij}(.) = \dot{G}(\alpha(x^{(2)}) + \beta(x^{(2)})'t_{i-1}t_{j-1}$, $t_i$ is the ith element of t, $i = 1, \ldots, K$, and $t_0 = 1$ for notation simplicity. Due to the symmetry of $\Lambda(.)$, $K(K+1)/2$ DNNs are used and each corresponds to an estimation of one element in a lower triangular part of $\Lambda(.)$.

The parameters of interest are estimated using $$\theta_0 = E(H(\{y, x^{(2)}, t\} \alpha(x^{(2)}), \beta(x^{(2)}), t^*))$$

where $\theta_0$ is the parameter of interest, $E(H(\{y, x^{(2)}, t\}, \alpha(x^{(2)}), \beta(x^{(2)}), t^*))$ is the conditional expectation function, $H(\{y, x^{(2)}, t\}, \alpha(x^{(2)}), \beta(x^{(2)}), t^*)$ is a predefined function, y is the outcome, t is the treatment, t* is a fixed value of interest such as a fixed benchmark treatment. For example, the ATE may be the parameter of interest. For ATE, the predefined function may be defined as $H(\{y, x^{(2)}, t\}, \alpha(x^{(2)}), \beta(x^{(2)}), t^*) = \beta(x^{(2)})$. Because the second set of covariates $x^{(2)}$ may have an effect on both the outcome and the treatment assignment, directly plugging in $\beta(x^{(2)})$ to determine the estimator $$\hat{\theta} = \frac{1}{n} \sum_{i=1}^{n} \hat{\beta}(x_i^{(2)})$$

of the parameter of interest may result in a highly biased estimator, where $x_i^{2)}$ is the second set of covariates with values for observation i, ^ indicates an estimator of the associated parameter, and n is a sample size. Instead, a doubly robust estimator with influence functions may be defined as $$\hat{\psi}(\{y_i, x_i^{(2)}, t_i\}, \hat{\alpha}(x_i^2), \hat{\beta}(x_i^{(2)}), t^*) =$$

$$H(\{y_i, x_i^{(2)}, t\}, \alpha(x_i^{(2)}), \beta(x_i^{(2)}), t^*) +$$

$$\Lambda H(.) \hat{\Lambda}(.)^{-1}(t_i^1)(y_i - G(\hat{\alpha}(x_i^{(2)}) + \hat{\beta}(x_i^{(2)})'t_i))$$

for each respective observation i, where $$\nabla H(.) = \left( \frac{\partial H}{\partial \alpha} \frac{\partial H}{\partial \beta_1} \cdots \frac{\partial H}{\partial \beta_K} \right)',$$

K is a dimension of treatment $t_i$, $\hat{\Lambda}(.)^{-1}$ is an inverse of an estimate of matrix function $\Lambda(.)$ computed using the matrix DNNs for the respective observation i or directly calculated through $p(x^{(1)})$ that is estimated by the treatment model.

The estimator for the parameter of interest may be defined as $$\hat{\theta} = \frac{\sum_{i=1}^{n} \hat{\psi}(x_i^{(2)}, \hat{\alpha}(x_i^{(2)}), \hat{\beta}(x_i^{(2)}), t^*)}{n}$$

with the standard error of $\hat{\theta}$ defined as $$\sigma(\hat{\theta}) = \frac{\sqrt{\sum_{i=1}^{n} (\hat{\psi}(\{y_i, x_i^{(2)}, t_i\}, \hat{\alpha}(x_i^{(2)}), \hat{\beta}(x_i^{(2)}), t^*) - \hat{\theta})^2}}{n}$$

The estimator is root-n-consistent such that $\sqrt{n}(\hat{\theta} - \theta_0) \to N(0, \Omega)$, where $\Omega = \text{cov}(\psi(\{y, x^{(2)}, t\}, \alpha(x^{(2)}), \beta(x^{(2)}), t^*))$, and $\theta_0$ is a true unknown parameter value. Root-n-consistent convergence means that even when the true value of $\theta_0$ is unknown, the estimate $\hat{\theta}$ still converges to the true value at a square-root-n rate. In other words, as the number of observations n increases, a distance between the true value $\theta_0$ and the estimated value $\hat{\theta}$ goes to zero quickly, as fast as $1/\sqrt{n}$.

Illustrative parameters of interest are provided in Table 1 below.

TABLE 1

| Parameter of Interest | Equation |
| --- | --- |
| $\mu_0$ | $E(Y(0))$ |
| $\mu_1$ | $E(Y(1))$ |
| ATE | $E(Y(1) - Y(0))$ |
| $\rho_{ij}$, i, j = 0,1 | $E(Y(i)|T = j)$ |
| ATT | $E(Y(1) - Y(0)|T = 1)$ |
| $\Delta_X$ | $E(Y(1)|T = 1) - E(Y(1)|T = 0)$ |
| $\Delta_\mu$ | $E(Y(1)|T = 0) - E(Y(0)|T = 0)$ |
| $\Delta$ | $E(Y(1)|T = 1) - E(Y(0)|T = 0)$ |

ATT indicates an average treatment effect for treated. Y(0) is a potential outcome, if the individual were untreated; whereas, Y(1) is the potential outcome, if the individual were treated.

When there are some confounders that cannot be observed, an instrument variable may be introduced into the outcome model for y and the treatment model for t, which can be defined as $$y = \alpha(x^{(2)}) + \beta(x^{(2)})t + v$$

$$t = \zeta_0(x^{(2)}) + \zeta_1(x^{(2)})z + u$$

where z indicates the instrument variable that has a direct effect on t but not on y, v is a disturbance error for the outcome model, u is a disturbance error for the treatment model, $\zeta_0$ and $\zeta_1$ are unknown functions that define the intercept and slope coefficients based on covariates $x^{(2)}$, and $E(v|x^{(2)}, z) = E(u|x^{(2)}, z) = 0$. Confounders are variables that impact both outcome variables and treatment variables. The instrument variable is included because some confounders cannot be observed, which implies that the u and v become correlated given $x^{(2)}$ alone. When conditional on z and $x^{(2)}$ together, u and v are not correlated and the relationship between y and t can be determined. A reduced form of the model can be defined as $$y = \tilde{\alpha}(x^{(2)}) + \tilde{\beta}(x^{(2)})z + \tilde{v}$$

$$\tilde{\alpha}(x^{(2)}) = \alpha(x_{(2)}) + \beta(x_{(2)})\zeta_0(x^{(2)})$$

$$\tilde{\beta}(x^{(2)}) = \beta(x^{(2)})\zeta_1(x^{(2)})$$

$$\tilde{v} = \beta(x^{(2)})u + v$$

~ where indicates a different unknown function.

In a second stage, policy optimization is performed. A policy, $\pi(x^{(3)})$, is a rule of assigning a treatment or defining a treatment value according to a third set of covariates $x^{(3)}$ of an observation. The policy DNN, whose input is $x^{(3)}$ and whose loss function may be a negative value function or a distance to a deduced optimized policy, is trained and applied to a new observation to assign a treatment value to the new observation. $x^{(3)}$ may be the same as or different from $x^{(1)}$ and/or $x^{(2)}$. The third set of covariates, $x^{(3)}$, may be referred to as the policy covariates. $x^{(1)} \cup x^{(2)}$ may have a high dimension, whereas, it may be desirable that the optimized policy be as simple as possible for better interpretability and lower cost. In that case, the third set of covariates $x^{(3)}$ may be a subset of the combination of the first set of covariates $x^{(1)}$ and the second set of covariates $x^{(2)}$. The third set of covariates $x^{(3)}$ may include additional covariates not included in the first set of covariates $x^{(1)}$ or the second set of covariates $x^{(2)}$. The third set of covariates $x^{(3)}$ may be defined by selecting the most important covariates from the first set of covariates $x^{(1)}$ and/or the second set of covariates $x^{(2)}$ in training and scoring the treatment model and the outcome model, respectively.

In policy optimization, the goal is to maximize a value function, $V(\pi(.))$. Assuming that the treatment t is binary, if a positive treatment effect is preferred, then anyone whose $\beta(x^{(3)})>0$ should be assigned the treatment. Although the true function $\beta(x_{(3)})$ is unknown, its estimator $\hat{\beta}(x^{(3)})$ may be sufficiently accurate to use in determining the treatment. As discussed below, simulation studies have shown that a mean squared error (MSE) of $\hat{\beta}(x^{(3)})$, $E(\|\hat{\beta}(x^{(3)})-\beta(x^{(3)})\|^2)=Bias^2+Variance$, is very small. Based on this, the optimized policy may be $\hat{\pi}(x^{(3)})=(\hat{\beta}(x^{(3)})>0)$. That is, $\hat{\pi}(x^{(3)})$ is 1, meaning the treatment is assigned, if $\hat{\beta}(x^{(3)})$ is positive; otherwise, $\hat{\pi}(x^{(3)})$ is 0, meaning the treatment is not assigned. As another illustration, when the outcome is a revenue, there is a fixed cost for each treatment, and the final goal is to maximize the profit, $\hat{\pi}(x^{(3)})=(\hat{\beta}(x^{(3)})>c/m)$, where c is the fixed cost of the treatment, and m is a profit margin. In the above two cases, the value function may be defined as $$V(\pi) = \frac{\sum_{i=1}^{n}(\pi(x_i^{(3)}) - (1-\pi(x_i^{(3)})))\hat{\beta}(x_i^{(3)})}{n}$$

and $$V(\pi) = \frac{\sum_{i=1}^{n}(\pi(x_i^{(3)}) - (1-\pi(x_i^{(3)})))(m\hat{\beta}(x_i^{(3)})-c)}{n},$$

respectively, which may be referred to as computing the value function using plug-in estimators where the plug-in estimator is $\hat{\beta}(x_i^{(3)})$ for these illustrative value functions.

In some cases, double robustness may be preferred. For example, when the treatment is binary and a positive treatment effect is preferred (e.g., the average outcome is the survival months), the value function may be defined as $$V(\pi) = \frac{\sum_{i=1}^{n}(\pi(x_i^{(3)}) - (1-\pi(x_i^{(3)})))\hat{\psi}(\{y_i, x_i^{(3)}, t_i\}, \hat{\alpha}(x_i^{(3)}), \hat{\beta}(x_i^{(3)}), t^*)}{n}$$

where $\hat{\psi}(.)$ is the influence function for the treatment effect corresponding to $H(\{y, x_i^{(3)}, t_i\}, \alpha(x_i^{(3)}), \beta(x_i^{(3)}), t^*)=\beta(x_i^{(3)})$. When the treatment is binary and a negative treatment effect is preferred (e.g., the average outcome is the mortality rate), the value function may be $$V(\pi) = -\frac{\sum_{i=1}^{n}(\pi(x_i^{(3)}) - (1-\pi(x_i^{(3)})))\hat{\psi}(\{y_i, x_i^{(3)}, t_i\}, \hat{\alpha}(x_i^{(3)}), \hat{\beta}(x_i^{(3)}), t^*)}{n}.$$

Employing double robustness may be referred to as computing the value function using the estimated influence function $\hat{\psi}(.)$.

The value function may be more complex. For example, when the treatment is the price (a continuous variable), the outcome is demand, and the final goal is to maximize the revenue, the value function may be defined as $$V(\pi) = \frac{1}{n}\sum_{i=0}^{n}\pi(x_i^{(3)})(\hat{\alpha}(x_i^{(3)}) + \hat{\beta}(x_i^{(3)})\pi(x_i^{(3)})).$$

Due to the relationship between price and demand in economics theory, $\hat{\beta}(x_i^{(3)})$ is negative for any $x^{(3)}$.

A policy DNN can be trained to use a negative value function as the loss function. However, for some value functions, the optimized policy can be directly determined from the estimates of $\hat{\alpha}(x)$ and $\hat{\beta}(x)$. Illustrative optimized policies that can be directly determined from the estimates of $\hat{\alpha}(x)$ and $\hat{\beta}(x)$ are shown in Table 2 below.

TABLE 2

| Value Function, $V(\pi)$ | Optimized Policy, $\pi(.)$ |
|---|---|
| $\frac{1}{n}\sum_{i=1}^{n}(\pi(x_i^{(3)}) - (1-\pi(x_i^{(3)})))\hat{\beta}(x_i^{(3)})$ | $\hat{\beta}(x_i^{(3)}) > 0$ |
| $\frac{1}{n}\sum_{i=1}^{n}(\pi(x_i^{(3)}) - (1-\pi(x_i^{(3)})))(m\hat{\beta}(x_i^{(3)})-c)$ | $\hat{\beta}(x_i^{(3)}) > c/m$ |
| $\frac{1}{n}\sum_{i=0}^{n}\pi(x_i^{(3)})(\hat{\alpha}(x_i^{(3)}) + \hat{\beta}(x_i^{(3)})\pi(x_i^{(3)}))$ | $-\frac{1}{2}\frac{\hat{\alpha}(x_i^{(3)})}{\hat{\beta}(x_i^{(3)})}$ |

Referring to FIG. 1, a block diagram of a model training device 100 is shown in accordance with an illustrative embodiment. Model training device 100 may include an input interface 102, an output interface 104, a communication interface 106, a non-transitory computer-readable medium 108, a processor 110, a causal inference and policy model application 122, input dataset 124, and a model description 126. Fewer, different, and/or additional components may be incorporated into model training device 100.

Input interface 102 provides an interface for receiving information from the user or another device for entry into model training device 100 as understood by those skilled in the art. Input interface 102 may interface with various input technologies including, but not limited to, a keyboard 112, a microphone 113, a mouse 114, a display 116, a track ball, a keypad, one or more buttons, etc. to allow the user to enter information into model training device 100 or to make selections presented in a user interface displayed on display 116.

The same interface may support both input interface 102 and output interface 104. For example, display 116 comprising a touch screen provides a mechanism for user input and for presentation of output to the user. Model training device 100 may have one or more input interfaces that use the same or a different input interface technology. The input interface technology further may be accessible by model training device 100 through communication interface 106.

Output interface 104 provides an interface for outputting information for review by a user of model training device 100 and/or for use by another application or device. For example, output interface 104 may interface with various output technologies including, but not limited to, display 116, a speaker 118, a printer 120, etc. Model training device 100 may have one or more output interfaces that use the same or a different output interface technology. The output interface technology further may be accessible by model training device 100 through communication interface 106.

Communication interface 106 provides an interface for receiving and transmitting data between devices using various protocols, transmission technologies, and media as understood by those skilled in the art. Communication interface 106 may support communication using various transmission media that may be wired and/or wireless. Model training device 100 may have one or more communication interfaces that use the same or a different communication interface technology. For example, model training device 100 may support communication using an Ethernet port, a Bluetooth antenna, a telephone jack, a USB port, etc. Data and/or messages may be transferred between model training device 100 and another computing device of a distributed computing system 130 using communication interface 106.

Computer-readable medium 108 is a non-transitory electronic holding place or storage for information so the information can be accessed by processor 110 as understood by those skilled in the art. Computer-readable medium 108 can include, but is not limited to, any type of random access memory (RAM), any type of read only memory (ROM), any type of flash memory, etc. such as magnetic storage devices (e.g., hard disk, floppy disk, magnetic strips, . . . ), optical disks (e.g., compact disc (CD), digital versatile disc (DVD), . . . ), smart cards, flash memory devices, etc. Model training device 100 may have one or more computer-readable media that use the same or a different memory media technology. For example, computer-readable medium 108 may include different types of computer-readable media that may be organized hierarchically to provide efficient access to the data stored therein as understood by a person of skill in the art. As an example, a cache may be implemented in a smaller, faster memory that stores copies of data from the most frequently/recently accessed main memory locations to reduce an access latency. Model training device 100 also may have one or more drives that support the loading of a memory media such as a CD, DVD, an external hard drive, etc. One or more external hard drives further may be connected to model training device 100 using communication interface 106.

Processor 110 executes instructions as understood by those skilled in the art. The instructions may be carried out by a special purpose computer, logic circuits, or hardware circuits. Processor 110 may be implemented in hardware and/or firmware. Processor 110 executes an instruction, meaning it performs/controls the operations called for by that instruction. The term "execution" is the process of running an application or the carrying out of the operation called for by an instruction. The instructions may be written using one or more programming language, scripting language, assembly language, etc. Processor 110 operably couples with input interface 102, with output interface 104, with communication interface 106, and with computer-readable medium 108 to receive, to send, and to process information. Processor 110 may retrieve a set of instructions from a permanent memory device and copy the instructions in an executable form to a temporary memory device that is generally some form of RAM. Model training device 100 may include a plurality of processors that use the same or a different processing technology.

Some machine-learning approaches may be more efficiently and speedily executed and processed with machine-learning specific processors (e.g., not a generic central processing unit (CPU)). Such processors may also provide additional energy savings when compared to generic CPUs. For example, some of these processors can include a graphical processing unit, an application-specific integrated circuit, a field-programmable gate array, an artificial intelligence accelerator, a purpose-built chip architecture for machine learning, and/or some other machine-learning specific processor that implements a machine learning approach using semiconductor (e.g., silicon, gallium arsenide) devices. These processors may also be employed in heterogeneous computing architectures with a number of and a variety of different types of cores, engines, nodes, and/or layers to achieve additional various energy efficiencies, processing speed improvements, data communication speed improvements, and/or data efficiency targets and improvements throughout various parts of the system.

Causal inference and policy model application 122 performs operations associated with defining model description 126 from data stored in input dataset 124. Model description 126 may be used to predict a treatment value for data stored in a second dataset 424 (shown referring to FIG. 4). Some or all of the operations described herein may be embodied in causal inference and policy model application 122. The operations may be implemented using hardware, firmware, software, or any combination of these methods.

Referring to the example embodiment of FIG. 1, causal inference and policy model application 122 is implemented in software (comprised of computer-readable and/or computer-executable instructions) stored in computer-readable medium 108 and accessible by processor 110 for execution of the instructions that embody the operations of causal inference and policy model application 122. Causal inference and policy model application 122 may be written using one or more programming languages, assembly languages, scripting languages, etc. Causal inference and policy model application 122 may be integrated with other analytic tools. As an example, causal inference and policy model application 122 may be part of an integrated data analytics software application and/or software architecture such as that offered by SAS Institute Inc. of Cary, N.C., USA. Merely for illustration, causal inference and policy model application 122 may be implemented using or integrated with one or more SAS software tools such as JMP®, Base SAS, SAS® Enterprise Miner™, SAS® Event Stream Processing, SAS/STAT®, SAS® High Performance Analytics Server, SAS® Visual Data Mining and Machine Learning, SAS® LASR™, SAS® In-Database Products, SAS® Scalable Performance Data Engine, SAS® Cloud Analytic Services (CAS), SAS/OR®, SAS/ETS®, SAS® Econometrics, SAS® Visual Analytics, SAS® Viya™, and SAS In-Memory Statistics for Hadoop®, etc. all of which are developed and provided by SAS Institute Inc. of Cary, N.C., USA. Data mining, statistical analytics, and response prediction are practically applied in a wide variety of industries to solve technical problems.

Causal inference and policy model application 122 may be implemented as a Web application. For example, causal inference and policy model application 122 may be configured to receive hypertext transport protocol (HTTP) responses and to send HTTP requests. The HTTP responses may include web pages such as hypertext markup language (HTML) documents and linked objects generated in response to the HTTP requests. Each web page may be identified by a uniform resource locator (URL) that includes the location or address of the computing device that contains the resource to be accessed in addition to the location of the resource on that computing device. The type of file or resource depends on the Internet application protocol such as the file transfer protocol, HTTP, H.323, etc. The file accessed may be a simple text file, an image file, an audio file, a video file, an executable, a common gateway interface application, a Java applet, an extensible markup language (XML) file, or any other type of file supported by HTTP.

Input dataset 124 may include, for example, a plurality of rows and a plurality of columns. The plurality of rows may be referred to as observation vectors or records (observations), and the columns may be referred to as variables. In an alternative embodiment, input dataset 124 may be transposed. The plurality of variables defines a vector $x_i$ for each observation vector i=1, 2, . . . , n, where n is a number of the observation vectors included in input dataset 124. Input dataset 124 may include additional variables that are not included in the plurality of variables. One or more variables of the plurality of variables may describe a characteristic of a physical object. For example, if input dataset 124 includes data related to operation of a vehicle, the variables may include a type of vehicle, an oil pressure, a speed, a gear indicator, a gas tank level, a tire pressure for each tire, an engine temperature, a radiator level, etc. The plurality of variables may include a plurality of covariates from which the first set of covariates $x^{(1)}$, the second set of covariates $x^{(2)}$, the third set of covariates $x^{(3)}$ and may include a treatment variable, an outcome variable, and an instrument variable.

In data science, engineering, and statistical applications, data often consists of multiple measurements (across sensors, characteristics, responses, etc.) collected across multiple time instances (patients, test subjects, etc.). These measurements may be collected in input dataset 124 for analysis and processing or streamed to model training device 100 as it is generated. Input dataset 124 may include data captured as a function of time for one or more physical objects. The data stored in input dataset 124 may be captured at different time points periodically, intermittently, when an event occurs, etc. Input dataset 124 may include data captured at a high data rate such as 200 or more observation vectors per second for one or more physical objects. One or more columns of input dataset 124 may include a time and/or date value. Input dataset 124 may include data captured under normal and abnormal operating conditions of the physical object.

The data stored in input dataset 124 may be received directly or indirectly from the source and may or may not be pre-processed in some manner. For example, the data may be pre-processed using an event stream processor such as the SAS® Event Stream Processing Engine (ESPE), developed and provided by SAS Institute Inc. of Cary, N.C., USA. For example, data stored in input dataset 124 may be generated as part of the Internet of Things (IoT), where things (e.g., machines, devices, phones, sensors) can be connected to networks and the data from these things collected and processed within the things and/or external to the things before being stored in input dataset 124. For example, the IoT can include sensors in many different devices and types of devices, and high value analytics can be applied to identify hidden relationships and drive increased efficiencies. This can apply to both big data analytics and real-time analytics. Some of these devices may be referred to as edge devices, and may involve edge computing circuitry. These devices may provide a variety of stored or generated data, such as network data or data specific to the network devices themselves. Again, some data may be processed with an ESPE, which may reside in the cloud or in an edge device before being stored in input dataset 124.

The data stored in input dataset 124 may include any type of content represented in any computer-readable format such as binary, alphanumeric, numeric, string, markup language, etc. The content may include textual information, graphical information, image information, audio information, numeric information, etc. that further may be encoded using various encoding techniques as understood by a person of skill in the art.

Input dataset 124 may be stored on computer-readable medium 108 or on one or more computer-readable media of distributed computing system 130 and accessed by model training device 100 using communication interface 106, input interface 102, and/or output interface 104. Input dataset 124 may be stored in various compressed formats such as a coordinate format, a compressed sparse column format, a compressed sparse row format, etc. The data may be organized using delimited fields, such as comma or space separated fields, fixed width fields, using a SAS® dataset, etc. The SAS dataset may be a SAS® file stored in a SAS® library that a SAS® software tool creates and processes. The SAS dataset contains data values that are organized as a table of observation vectors (rows) and variables (columns) that can be processed by one or more SAS software tools.

Input dataset 124 may be stored using various data structures as known to those skilled in the art including one or more files of a file system, a relational database, one or more tables of a system of tables, a structured query language database, etc. on model training device 100 or on distributed computing system 130. Model training device 100 may coordinate access to input dataset 124 that is distributed across distributed computing system 130 that may include one or more computing devices. For example, input dataset 124 may be stored in a cube distributed across a grid of computers as understood by a person of skill in the art. As another example, input dataset 124 may be stored in a multi-node Hadoop® cluster. For instance, Apache™ Hadoop® is an open-source software framework for distributed computing supported by the Apache Software Foundation. As another example, input dataset 124 may be stored in a cloud of computers and accessed using cloud computing technologies, as understood by a person of skill in the art. The SAS® LASR™ Analytic Server may be used as an analytic platform to enable multiple users to concurrently access data stored in input dataset 124. The SAS Viya open, cloud-ready, in-memory architecture also may be used as an analytic platform to enable multiple users to concurrently access data stored in input dataset 124. SAS CAS may be used as an analytic server with associated cloud services in SAS Viya. Some systems may use SAS In-Memory Statistics for Hadoop® to read big data once and analyze it several times by persisting it in-memory for the entire session. Some systems may be of other types and configurations.

Figure 2A:
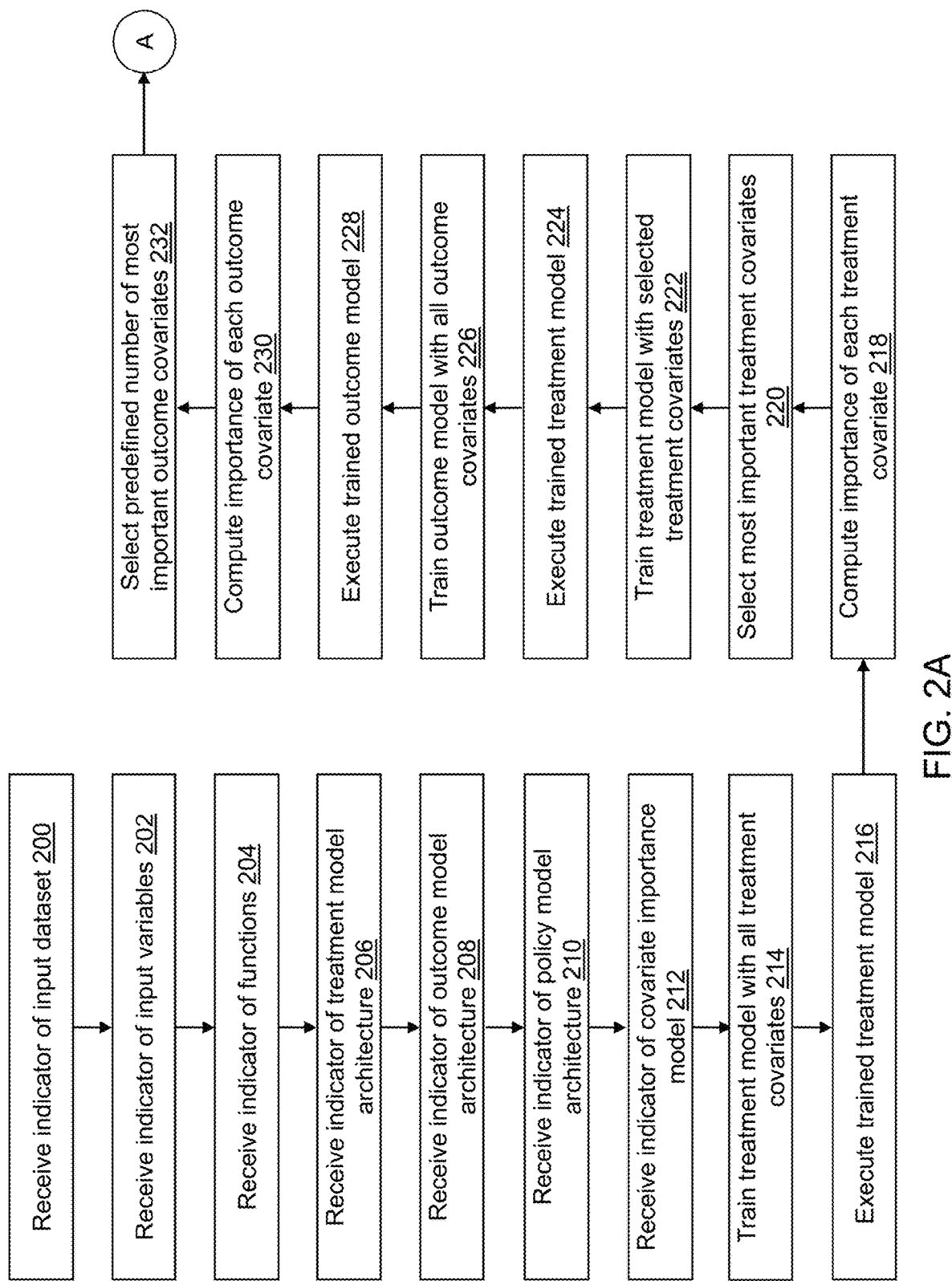
FIGS. 2A and 2B depict a flow diagram illustrating examples of operations performed by a causal inference and policy model training application of the model training device of FIG. 1 in accordance with an illustrative embodiment.
Figure 2B:
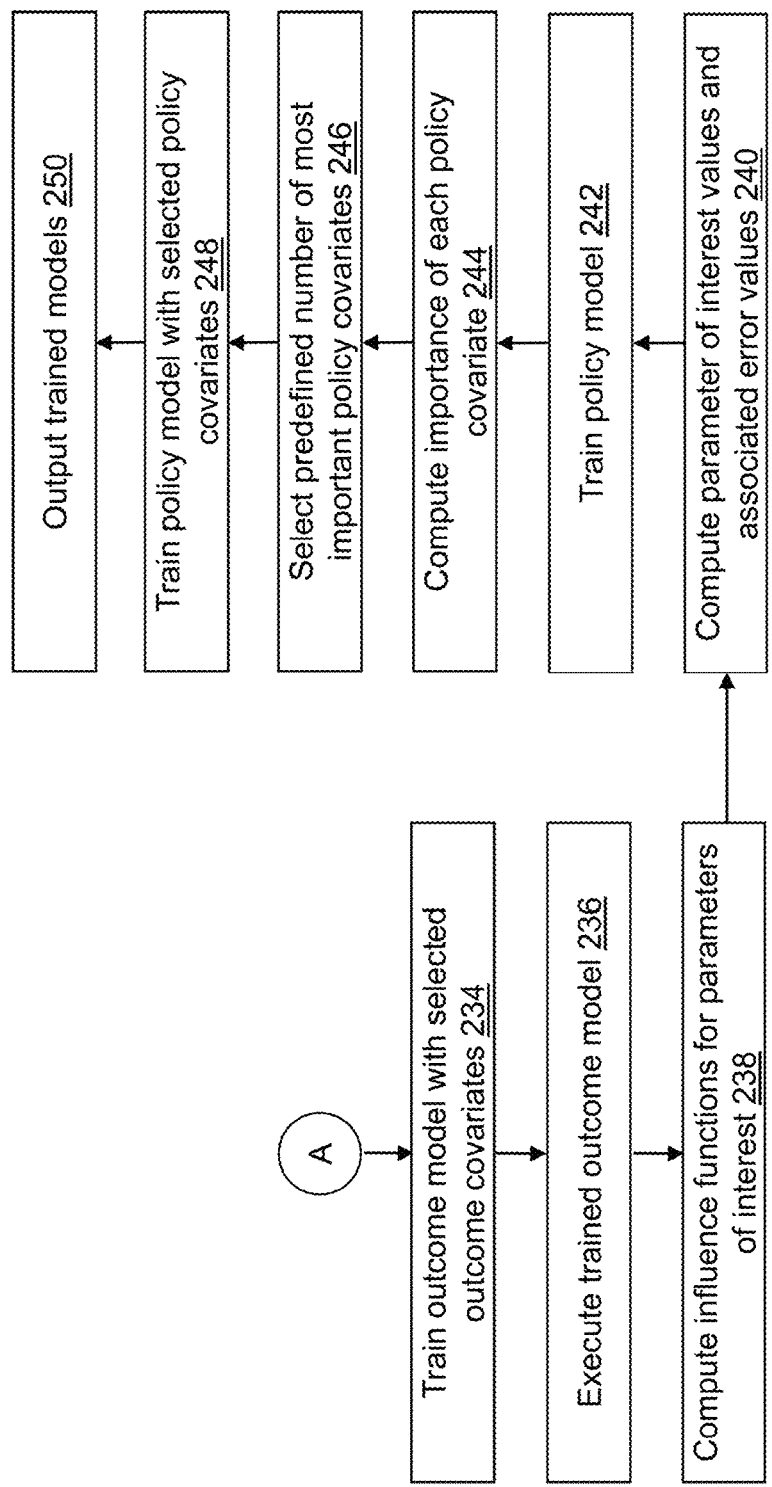

Referring to FIGS. 2A and 2B, example operations associated with causal inference and policy model application 122 are described. Additional, fewer, or different operations may be performed depending on the embodiment of causal inference and policy model application 122. The order of presentation of the operations of FIGS. 2A and 2B is not intended to be limiting. Some of the operations may not be performed in some embodiments. Although some of the operational flows are presented in sequence, the various operations may be performed in various repetitions and/or in other orders than those that are illustrated. For example, a user may execute causal inference and policy model application 122, which causes presentation of a first user interface window, which may include a plurality of menus and selectors such as drop-down menus, buttons, text boxes, hyperlinks, etc. associated with causal inference and policy model application 122 as understood by a person of skill in the art. The plurality of menus and selectors may be accessed in various orders. An indicator may indicate one or more user selections from a user interface, one or more data entries into a data field of the user interface, one or more data items read from computer-readable medium 108 or otherwise defined with one or more default values, etc. that are received as an input by causal inference and policy model application 122. The operations of causal inference and policy model application 122 further may be performed in parallel using a plurality of threads and/or a plurality of worker computing devices.

Referring to FIG. 2A, in an operation 200, a first indicator may be received that indicates input dataset 124. For example, the first indicator indicates a location and a name of input dataset 124. As an example, the first indicator may be received by causal inference and policy model application 122 after selection from a user interface window or after entry by a user into a user interface window. In an alternative embodiment, input dataset 124 may not be selectable. For example, a most recently created dataset may be used automatically. As understood by a person of skill in the art, input dataset 124 may be partitioned or otherwise divided into training, validation, and/or test datasets as part of training a neural network model and executing the trained neural network model to compute a performance score.

In an operation 202, a second indicator may be received that indicates a plurality of variables or features to include in training a neural network model using input dataset 124. For example, the second indicator may indicate a column number(s) or a column name(s) used to define each of the first set of covariates $x^{(1)}$, the second set of covariates $x^{(2)}$, the third set of covariates $x^{(3)}$, the treatment variable t, the outcome variable y, and the instrument variable z.

In an operation 204, a third indicator may be received that indicates the functions for $G(\alpha(x^{(2)})+\beta(x^{(2)})'t)$, $H(\{y, x^{(2)}, t\}, \alpha(x^{(2)}), \beta(x^{(2)}), t^*)$, $V(\pi(.))$, and one or more of the parameters of interest listed in Table 1 above. In some cases, the third indicator may further indicate a derivative or gradient of the functions for $G(\alpha(x^{(2)})+\beta(x^{(2)})'t)$ and $H(\{y, x^{(2)}, t\}, \alpha(x^{(2)}), \beta(x^{(2)}), t^*)$ such as $\nabla H(.)$. For illustration, G may be the identity function such that $G(u)=u$ or a logit function $$G(u) = \frac{1}{1+e^{-u}}.$$

For illustration, H may be $H(\{y, x^{(2)}, t\}, \alpha(x^{(2)}), \beta(x^{(2)}), t^*)=\alpha(x^{(2)})$, $H(\{y, x^{(2)}, t\}, \alpha(x^{(2)}), \beta(x^{(2)}), t^*)=\beta(x^{(2)})$, or a partial average treatment effect. For illustration, V may be $$V(\pi) = \frac{\sum_{i=1}^{n}(\pi(x_i^{(3)})-(1-\pi(x_i^{(3)})))\hat{\beta}(x_i^{(3)})}{n}.$$

Based on the indicated $V(\pi(.))$, the value function may be computed using plug-in estimators or the estimated influence function $\psi(.)$.

In an operation 206, a fourth indicator indicates an architecture of the treatment model to be trained to regress t on $x^{(1)}$,z to estimate $\hat{p}(x^{(1)})$, $\hat{t}$, $\hat{\zeta}_0(x^{(1)})$, and $\hat{\zeta}_1(x^{(1)})$ for each observation, where $\hat{p}(x^{(1)})$ is an estimate of the treatment assigning probability conditioned on the first set of covariates. The fourth indicator may be received by causal inference and policy model application 122 from a user interface window or after entry by a user into a user interface window. A default value for the architecture may further be stored, for example, in computer-readable medium 108. For the treatment model, a negative log likelihood function is an illustrative loss function though other loss functions may be indicated or otherwise used. For illustration, the architecture defines a plurality of layers and their connectivity including a type of each layer. Illustrative layers include an input layer, a convolution layer, a rectified linear activation function (ReLU) layer, a pooling layer, an output layer, etc. A ReLU layer is a piecewise linear function that outputs the input directly if it is positive, and outputs zero otherwise. One or more hyperparameters may be defined for each layer that may vary based on a type of each layer. For example, an activation function, a number of neurons, a number of groups, a dropout rate, a height and/or a width of a convolution window, a number of filters, an initialization method for filter weights, width and height padding dimensions, a number of categories or labels or unique values of the target variable value $y_i$, a detection threshold, etc. may be defined as hyperparameters for training the neural network. The architecture may define a convolutional neural network, a DNN, and/or a recurrent neural network. An automatic tuning method (autotune option) may be specified with one or more values or ranges of values to evaluate for each hyperparameter. The automatic tuning process may be used to identify the best settings for the hyperparameters though the hyperparameters may optionally be selected as an input option by a user without tuning. For illustration, an automatic tuning process is described in U.S. Pat. Nos. 10,360,517; 10,600,005; 10,832,174; and 11,093,833. A deep learning action set provided as part of SAS® Viya 3.4 may be used to build the treatment model and add layers to the treatment model. An illustrative treatment model is defined in Appendix A that accompanies this application filing. In general, the treatment model includes an input layer that provides $x^{(1)}$ to hidden layers with the same or a different number of nodes on each hidden layer. A last layer of the hidden layers provides input to an output layer that computes a predicted treatment value that may be a predicted probability of assigning the treatment (e.g., when the treatment is binary or discrete).

In an operation 208, a fifth indicator indicates an architecture of the outcome model to be trained to regress y on $x^{(2)}$ and t ort to estimate $\hat{\alpha}(x^{(2)})$ and $\hat{\beta}(x^{(2)})$ for each observation. When there are no unobserved confounders and thus no instrument variable z, t is used to regress y on $x^{(2)}$ and t, and $\hat{\alpha}(x^{(2)})$ and $\hat{\beta}(x^{(2)})$ are estimated for each observation. When there are unobserved confounders and there is an instrument variable z, regress y on $x^{(2)}$ and $\hat{t}$, and $\hat{\alpha}(x^{(2)})$ and $\hat{\beta}(x^{(2)})$ are estimated for each observation, where t is estimated from the treatment model that regresses t on $x^{(1)}$,z. The fifth indicator may be received by causal inference and policy model application 122 from a user interface window or after entry by a user into a user interface window. A default value for the architecture may further be stored, for example, in computer-readable medium 108. For illustration, the architecture defines a plurality of layers and their connectivity including a type of each layer. The architecture may define a convolutional neural network, a DNN, and/or a recurrent neural network. For the outcome model, a squared error function is an illustrative loss function though other loss functions may be indicated or otherwise used. An automatic tuning method (autotune option) may be specified with one or more values or ranges of values to evaluate for each hyperparameter. The automatic tuning process may be used to identify the best settings for the hyperparameters though the hyperparameters may optionally be selected as an input option by a user. An illustrative outcome model is defined in Appendix A that accompanies this application filing.

Figure 3:
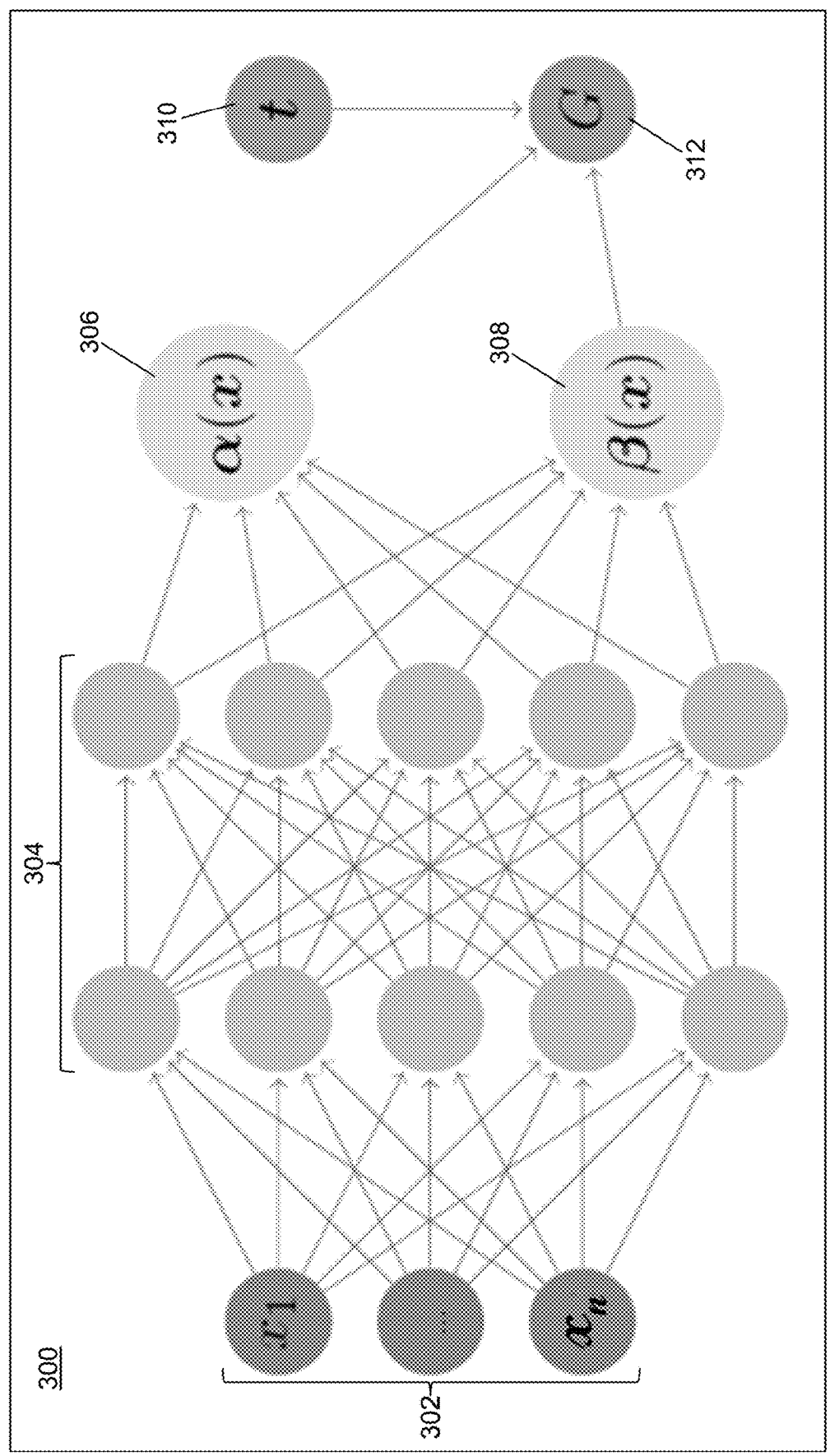
FIG. 3 depicts an illustrative neural network architecture for an outcome model of the causal inference and policy model training application in accordance with an illustrative embodiment.

For further illustration, referring to FIG. 3, an architecture 300 is shown in accordance with an illustrative embodiment for the outcome model. Architecture 300 is described in FIG. 1 of a paper tilted *Deep Learning for Individual Heterogeneity* by M. H. Farrell, T. Liang, and S. Misra and published Oct. 29, 2020 at arXiv:2010.14694v1 (*FLM paper*). Architecture 300 includes an input layer 302 that includes each covariate of the second set of covariates $x^{(2)}$. The input layer is connected to a plurality of fully connected hidden layers 304. A last layer of the plurality of fully connected hidden layers 304 is connected to provide input to an $\alpha$ parameter layer 306 and to a $\beta$ parameter layer 308. The $\alpha$ parameter layer 306 and the $\beta$ parameter layer 308 are connected to provide input to a G function layer 312. A t input layer 310 is also connected to provide input to G function layer 312 to optimize the outcome estimate $y=G(\alpha(x^{(2)})+\beta(x^{(2)})'t)$. A measure of the error in terms of an objective function is fed back to drive the adjustment of weights associated with each neuron of architecture 300. Gradients may be computed each iteration through back propagation through the architecture and also used to drive the adjustment of weights associated with each neuron of architecture 300 as the outcome model is trained. In the *FLM paper*, when there are unobserved confounders and there is an instrument variable z, y is regressed on $x^{(2)}$ and z, and $\hat{\tilde{\alpha}}(x^{(2)})$ and $\hat{\tilde{\beta}}(x^{(2)})$ are estimated for each observation. $\hat{\alpha}(x^{(2)})$ and $\hat{\beta}(x^{(2)})$ are computed from $\hat{\tilde{\alpha}}(x^{(2)})$ and $\hat{\tilde{\beta}}(x^{(2)})$ using $$\hat{\beta}(x^{(2)}) = \frac{\hat{\tilde{\beta}}(x^{(2)})}{\hat{\zeta}_1(x^{(2)})}$$

and $\hat{\alpha}(x^{(2)})=\hat{\tilde{\alpha}}(x^{(2)})-\hat{\beta}(x^{(2)})\hat{\zeta}_0(x^{(2)})$, where $\hat{\zeta}_1(x^{(2)})$ and $\hat{\zeta}_0(x^{(2)})$ is determined from the treatment model that regresses t on $x^{(1)}$, z when we assume that $x^{(2)}=x^{(1)}$ to simplify the notation.

Referring again to FIG. 2A, in an operation 210, a sixth indicator indicates an architecture of the policy model to be trained to maximize the value function indicated in operation 204 on $x^{(3)}$, $\hat{\alpha}(x^{(3)})$, and $\hat{\beta}(x^{(3)})$ to estimate $\hat{\pi}(x^{(3)})$ for each observation. The sixth indicator may be received by causal inference and policy model application 122 from a user interface window or after entry by a user into a user interface window. A default value for the architecture may further be stored, for example, in computer-readable medium 108. For illustration, the architecture defines a plurality of layers and their connectivity including a type of each layer. The architecture may define a convolutional neural network, a DNN, and/or a recurrent neural network. An automatic tuning method (autotune option) may be specified with one or more values or ranges of values to evaluate for each hyperparameter. The automatic tuning process may be used to identify the best settings for the hyperparameters though the hyperparameters may optionally be selected as an input option by a user. An illustrative policy model is defined in Appendix A that accompanies this application filing In an operation 212, a seventh indicator of a covariate importance model may be received. The covariate importance model computes a measure of importance for each covariate in training one or more of the treatment model, the outcome model, and the policy model though the covariate importance model may not be indicated for any of the treatment model, the outcome model, and the policy model. The seventh indicator may further indicate whether the covariate importance model is applied to the treatment model, the outcome model, and/or the policy model. The same or a different covariate importance model may be applied to each indicated model. When applied to one or more of the models, the one or more models may be retrained with only the covariates for which the computed measure of importance is greater than an importance threshold defined using the seventh indicator or with only the covariates for which an importance rank determined using the computed measure of importance indicates the covariate rank is less than an importance rank threshold defined using the seventh indicator. Relative to the policy model, the seventh indicator may further indicate that the policy model is trained with a first number of covariates selected from the first set of covariates $x^{(1)}$ based on the measured importance of each covariate included in $x^{(1)}$ in training the treatment model and/or that the policy model is trained with a second number of covariates selected from the second set of covariates $x^{(2)}$ based on the measured importance of each covariate included in $x^{(2)}$ in training the outcome model. In an alternative embodiment, the seventh indicator may not be received. For example, a default covariate importance model may be stored, for example, in computer-readable medium 108 and used automatically. In another alternative embodiment, the covariate importance model may not be selectable. Instead, a fixed, predefined covariate importance model may be used or no covariate importance model may be used.

For illustration, the covariate importance model may compute a loss function value for the indicated trained model (treatment model, outcome model, policy model) with successive sets of covariates that leave out covariate values for one of the covariates of the respective sets of covariates $x^{(1)}$, $x^{(2)}$, $x^{(3)}$, where each covariate is left out of a single set of covariates. A distance value, such as a mean square error value, may be computed between the loss function value computed using the full set of covariates and the loss function value computed using each of the sets of covariates with a single covariate left out. The distance value may be stored as the importance measure in association with the covariate left out of each respective set of covariates, where the larger the distance value is, the more important the covariate is. A rank may be determined by sorting the covariates based on the importance measure from a largest value to a smallest value.

In an operation 214, the treatment model defined by the architecture specified in operation 206 is trained with a treatment variable value $t_i$, covariate values for the first set of covariates $x_i^{(1)}$, and an instrument variable value $z_i$ read from input dataset 124 for each observation vector i of the n observation vectors to regress t on $x^{(1)}$, z to estimate $\hat{p}(x^{(1)})$, $\hat{t}$, $\hat{\zeta}_1(x^{(1)})$, and $\hat{\zeta}_1(x^{(1)})$ for each observation vector of the n observation vectors. In an illustrative embodiment, a subset of the n observation vectors included in input dataset 124 are selected as a training dataset that is input to train the treatment model instead of the entire input dataset 124.

The first set of covariates $x^{(1)}$ are the variables input to the input layer of the treatment model. The output layer computes the predicted treatment value. The training process optimizes the loss function based on the target variable, which is the treatment variable t that is the predicted treatment value.

In an operation 216, the trained treatment model is executed with the covariate values for the first set of covariates $x^{(1)}$ and the instrument variable value z read from input dataset 124 for each observation vector of the n observation vectors to compute the treatment variable value t for each observation vector of the n observation vectors. In an illustrative embodiment, a subset of the n observation vectors included in input dataset 124 are selected as a testing dataset that is input to the trained treatment model instead of the entire input dataset 124. An objective function value is computed based on a comparison between the predicted treatment variable value $\hat{t}_i$ and the treatment variable value $t_i$ read from input dataset 124.

In an operation 218, an importance value is computed for each covariate of the first set of covariates $x^{(1)}$ using the covariate importance model indicated in operation 212 for the treatment model, if any was indicated.

In an operation 220, the most important covariates of the first set of covariates $x^{(1)}$ are selected based on the computed importance value. For example, the most important covariates of the first set of covariates $x^{(1)}$ may be selected based on the importance threshold or the importance rank indicated in operation 212 for the treatment model.

Similar to operation 214, in an operation 222, the treatment model defined by the architecture specified in operation 206 is trained with a treatment variable value $t_i$, covariate values for the selected most important covariates, and the instrument variable value $z_i$ read from input dataset 124 for each observation vector i of the n observation vectors. Again, in an illustrative embodiment, the training dataset may be used instead of the entire input dataset 124.

Similar to operation 216, in an operation 224, the treatment model trained in operation 222 is executed with the covariate values for the selected most important covariates and the instrument variable value z read from input dataset 124 for each observation vector of the n observation vectors to compute the estimated treatment variable value $\hat{t}$ for each observation vector of the n observation vectors. Again, in an illustrative embodiment, the testing dataset may be used instead of the entire input dataset 124.

When the covariate importance model is not indicated in operation 212 for the treatment model and the policy model is not indicated in operation 212 to use the first number of covariates selected from the first set of covariates $x^{(1)}$, operations 218 through 224 may not be performed. When the covariate importance model is not indicated in operation 212 for the treatment model and the policy model is indicated in operation 212 to use the first number of covariates selected from the first set of covariates $x^{(1)}$, operations 222 through 224 may not be performed such that the treatment model is not retrained.

In an operation 226, the outcome model defined by the architecture specified in operation 208 is trained with the outcome variable value $y_i$ and covariate values for the second set of covariates $x_i^{(2)}$ read from input dataset 124 for each observation vector i of the n observation vectors to regress y on $x^{(2)}$ and the estimated treatment variable value $\hat{t}$ to estimate $\hat{\alpha}(x^{(2)})$ and $\hat{\beta}(x^{(2)})$ for each observation vector of the n observation vectors. Again, in an illustrative embodiment, the training dataset may be used instead of the entire input dataset 124.

The second set of covariates $x^{(2)}$ are the variables input to the input layer of the outcome model. A last layer of the hidden layers is connected to model layers for the complex models with the goal of generating the estimated outcome $\hat{y}$ according to the equation $G(\alpha(x^{(2)}) + \beta(x^{(2)})t)$. The output layer computes the estimated (discrete or continuous) outcome $\hat{y}_i$ for each observation vector i of the n observation vectors. The training process optimizes the loss function based on the target variable, which is the outcome variable y.

In an operation 228, the trained outcome model is executed with the covariate values for the second set of covariates $x^{(2)}$ read from input dataset 124 for each observation vector of the n observation vectors and the estimated treatment variable value $\hat{t}$ to compute the outcome variable y for each observation vector of the n observation vectors. Again, in an illustrative embodiment, the testing dataset may be used instead of the entire input dataset 124. An objective function value is computed based on a comparison between the estimated outcome variable value $\hat{y}_i$ and the outcome variable value $y_i$ read from input dataset 124. To compute the predicted outcome variable value $\hat{y}_i$, $\hat{y}_i = \hat{\alpha}(x_i^{(2)}) + \hat{\beta}(x_i^{(2)})\hat{t}$. Using the method described in the *FLM paper*, to compute the predicted outcome variable value $\hat{y}_i$, $\tilde{\alpha}(x_i^{(2)}) = \hat{\alpha}(x_i^{(2)}) + \hat{\beta}(x_i^{(2)})\hat{\xi}_0(x_i^{(2)})$, $\tilde{\beta}(x_i^{(2)}) = \hat{\beta}(x_i^{(2)})\hat{\xi}_1(x_i^{(2)})$, and $\tilde{v} = \hat{\beta}(x_i^{(2)})u + v$ are computed, where $\hat{y}_i = \tilde{\alpha}(x_i^{(2)}) + \tilde{\beta}(x_i^{(2)})z + \tilde{v}$.

In an operation 230, an importance value is computed for each covariate of the second set of covariates $x^{(2)}$ using the covariate importance model indicated in operation 212 for the outcome model, if any was indicated.

In an operation 232, the most important covariates of the second set of covariates $x^{(2)}$ are selected based on the computed importance value. For example, the most important covariates of the second set of covariates $x^{(2)}$ may be selected based on the importance threshold or the importance rank indicated in operation 212 for the outcome model. Processing continues with operation 234 shown referring to FIG. 2B.

Similar to operation 226, in operation 234, the outcome model defined by the architecture specified in operation 206 is trained with an outcome variable value $y_i$ and covariate values for the most important covariates selected in operation 232 read from input dataset 124 for each observation vector i of the n observation vectors and with the estimated treatment variable value $\hat{t}$. Again, in an illustrative embodiment, the training dataset may be used instead of the entire input dataset 124.

Similar to operation 228, in an operation 236, the outcome model trained in operation 222 is executed with the covariate values for the most important covariates selected in operation 232 and the instrument variable value z read from input dataset 124 for each observation vector of the n observation vectors to compute the outcome variable value $\hat{y}$ for each observation vector of the n observation vectors. Again, in an illustrative embodiment, the testing dataset may be used instead of the entire input dataset 124.

When the covariate importance model is not indicated in operation 212 for the outcome model and the policy model is not indicated in operation 212 to use the second number of covariates selected from the second set of covariates $x^{(2)}$, operations 230 through 236 may not be performed. When the covariate importance model is not indicated in operation 212 for the outcome model and the policy model is indicated in operation 212 to use the second number of covariates selected from the second set of covariates $x^{(2)}$, operations 234 and 236 may not be performed such that the outcome model is not retrained.

In an operation 238, an influence function value is computed for each parameter of interest indicated in operation 204 based on $\hat{\psi}(\{y_i, x_i^{(2)}, t_i\}, \hat{\alpha}(x_i^2), \hat{\beta}(x_i^{(2)}), t^*) = H(\{y_i, x_i^{(2)} t_i\}, \alpha(x_i^{(2)}), \beta(x_i^{(2)}), t^*) + \nabla H(.)\hat{\Lambda}(.)^{-1} (t_i^1)(y_i - G(\hat{\alpha}(x_i^{(2)}) + \hat{\beta}(x_i^{(2)})'t_i))$, where $H( )$, $\nabla H(.)$, and $G( )$ are predefined functions defined based on the parameters of interest indicated in operation 204, and $\hat{\Lambda}(.)^{-1}$ is computed from the matrix function $\Lambda(.)$ that is estimated using $p(x^{(1)})$ estimated by the treatment model or by training and executing the K(K+1)/2 matrix DNNs. For example, the influence function value for each parameter of interest may be computed using equation 7.5 described in section 7.1 of a paper titled *Deep Learning for Individual Heterogeneity* by M. H. Farrell, T. Liang, and S. Misr and published Oct. 29, 2020 at arXiv: 2010.14694v1 (*FLM paper*) using $\hat{\tilde{\alpha}}(x_i^{(2)})$ and $\hat{\tilde{\beta}}(x_i^{(2)})$, where $\hat{\tilde{\alpha}}(x_i^{(2)}) = \hat{\alpha}(x_i^{(2)}) + \hat{\beta}(x_i^{(2)})\hat{\zeta}_0$ $(x_i^{(2)})$ and $\hat{\tilde{\beta}}(x_i^{(2)}) = \hat{\beta}(x_i^{(2)})\hat{\zeta}_1(x_i^{(2)})$ may be computed. Illustrative computations are further described in a section *Estimating Parameters of Interest* included in SAS® Econometrics Procedures 2021 Jan. 4* published Aug. 18, 2021 by SAS Institute Inc.

In an operation 240, a parameter of interest value for each parameter of interest indicated in operation 204 is computed by dividing the sum of the respective influence function value by n. As a result, the parameter of interest value is a sample mean of the influence function value. A standard error for each parameter of interest indicated in operation 204 is computed by dividing a square root of the sum of the respective influence function value by n.

In an operation 242, the policy model defined by the architecture specified in operation 210 is trained with an outcome variable value $y_i$, covariate values for the third set of covariates $x_i^{(3)}$, and the instrument variable value $z_i$ read from input dataset 124 for each observation vector i of the n observation vectors to maximize the value function indicated in operation 204 on $x(x_i^{(2)})$, $\hat{\alpha}(x_i^{(3)})$, and $\hat{\beta}(x_i^{(3)})$, and the influence functions to estimate $\hat{\pi}(x^{(3)})$ for each observation vector of the n observation vectors. Again, in an illustrative embodiment, the training dataset may be used instead of the entire input dataset 124. When the deduced optimized policy is available, for example as listed in Table 2 above, the policy model is trained with the deduced optimized policy as a target. Otherwise, the policy model may be trained with a negative of the value function as a loss function.

The third set of covariates $x^{(3)}$ are the variables input to the input layer of the policy model. In an alternative embodiment, when the policy model is indicated in operation 212 to use the first number of covariates selected from the first set of covariates $x^{(1)}$, the most important covariates of the first set of covariates $x^{(1)}$ are the variables input to the input layer, and/or, when the policy model is indicated in operation 212 to use the second number of covariates selected from the second set of covariates $x^{(2)}$, the most important covariates of the second set of covariates $x^{(2)}$ are also, or alternatively, the variables input to the input layer. The output layer defines $\hat{\pi}(x^{(3)})$.

In an operation 244, an importance value is computed for each covariate of the third set of covariates $x^{(3)}$ using the covariate importance model indicated in operation 212 for the policy model, if any was indicated.

In an operation 246, the most important covariates of the third set of covariates $x^{(3)}$ are selected based on the computed importance value. For example, the most important covariates of the third set of covariates $x^{(3)}$ may be selected based on the importance threshold or the importance rank indicated in operation 212 for the policy model.

Similar to operation 244, in an operation 248, the policy model defined by the architecture specified in operation 210 is trained with a treatment variable value $t_i$, an outcome variable value $y_i$, covariate values for the most important covariates selected in operation 246, and the instrument variable value $z_i$ read from input dataset 124 for each observation vector i of the n observation vectors. Again, in an illustrative embodiment, the training dataset may be used instead of the entire input dataset 124. When the covariate importance model is not indicated in operation 212 for the policy model, operations 244 through 248 may not be performed.

In an operation 250, the trained policy model, the trained outcome model, and/or the trained treatment model are output. For example, the trained policy model, the trained outcome model, and/or the trained treatment model may be output to model description 126. The trained policy model, the trained outcome model, and/or the trained treatment model may include a respective neural network architecture indicated in operation 206, operation 208, and/or operation 210. For illustration, the trained models may be stored using the ASTORE procedure provided by SAS® Visual Data Mining and Machine Learning software. Additional parameter values may be output such as the parameter of interest values and their associated error values, as well as the parameters estimated using the treatment model and/or the outcome model. For example, the additional parameter values may be output to a table, to display 116, etc.

A first experiment was conducted in which the treatment variable was binary and the outcome variable was continuous. Details related to the first experiment are included in Appendix A. $G(.)$ was selected as the identity function. In the randomly generated data, there were 20 covariates, $x_j \sim \text{Uniform}(0,1)$, $j=1, \ldots, 20$. Four of them, $x_{s_i}$, $i=1, \ldots, 4$, were randomly selected and used in the outcome model:

$$Y = \alpha(x) + \beta(x)t + \varepsilon, \varepsilon \sim_{iid} N(0, 1)$$

$$\alpha(x) = 1 + \cos\left(2\pi \sum_{i=1}^{4} w_i x_{s_i}\right)$$

$$\beta(x) = \sin\left(2\pi \sum_{i=1}^{4} w_i x_{s_i}\right)$$

The propensity score model was $\text{Prob}\{T=1|X=x\} = p(x) = 0.1 + 0.8 \sin(2\pi|x_{s_1} - 0.5|)$.

20,000 observations were generated. The first 10,000 observations were used as the training dataset, and the remaining 10,000 observations were used as the testing dataset. The unknown functions $p(.)$, $\alpha(.)$, and $\beta(.)$ were estimated using two DNNs. Covariate importance was not used to retrain the treatment model or the outcome model. Table 3 below includes the results of the estimation of the unknown functions by the two DNNs using the training dataset.

TABLE 3

|  | Bias | Variance | MSE | Original Variance | $R^2$ |
| --- | --- | --- | --- | --- | --- |
| $\alpha(.)$ | −0.0064 | 0.0107 | 0.0107 | 0.1624 | 0.9339 |
| $\beta(.)$ | 0.0022 | 0.0117 | 0.0117 | 0.4323 | 0.9729 |
| $p(.)$ | −0.0100 | 0.0044 | 0.0045 | 0.0605 | 0.9263 | where MSE indicates the mean square error. Table 4 below includes the result of the estimation of the unknown functions by the two DNNs using the testing dataset.

TABLE 4

|       | Bias    | Variance | MSE    | Original Variance | $R^2$  |
|-------|---------|----------|--------|-------------------|--------|
| α(.)  | −0.0059 | 0.0110   | 0.0110 | 0.1632            | 0.9326 |
| β(.)  | 0.0037  | 0.0124   | 0.0124 | 0.4299            | 0.9712 |
| p(.)  | −0.0100 | 0.0046   | 0.0047 | 0.0608            | 0.9235 |

The results show that the estimates are very accurate using both the training and the testing datasets.

The parameters of interest indicated in Table 1 were computed. Table 5 below includes the estimated value and the associated standard error for each parameter of interest.

TABLE 5

| Parameter of interest | Estimated value | Standard Error |
|-----------------------|-----------------|----------------|
| $\mu_0$               | 0.33276         | 0.02210        |
| $\mu_1$               | 0.36886         | 0.01671        |
| ATE                   | 0.03610         | 0.02707        |
| $\rho_{00}$           | 0.36355         | 0.01769        |
| $\rho_{01}$           | 0.31228         | 0.02973        |
| $\rho_{10}$           | 0.38744         | 0.02535        |
| $\rho_{11}$           | 0.35650         | 0.01664        |
| ATT                   | 0.04422         | 0.03301        |
| $\Delta_X$            | −0.03094        | 0.02449        |
| $\Delta_\mu$          | 0.02389         | 0.02886        |
| $\Delta$              | −0.00705        | 0.02481        |

All of the parameter estimates are very accurate in comparison to the known values based on the small standard errors.

Two oracle policies were used that corresponded to the best and worst policies, respectively, when the positive, or negative, treatment effect is preferred. The third set of covariates $x^{(3)}$ input to the policy model DNN were the four most important covariates selected in operation 232 based on the trained outcome model. The deduced optimized policy was $\pi(x)=(\hat{\beta}(x)>0)$. Table 6 below includes the results of the two policies.

TABLE 6

| Policy | Estimated value | Standard Error |
|--------|-----------------|----------------|
| s0     | 0.058269        | 0.019388       |
| s1     | 0.643346        | 0.019352       |

Both policies resulted in small standard errors. The two policies were compared with an observed policy that assigns the treatment as indicated in the observed data. Table 7 below includes the comparison results to the observed policy. The result shows that s0 and t are significantly different and, in average for each individual, s0 policy has about −0.3 outcome than the observed policy π. Similarly, s1 and π are also significantly different but, in average for each individual, s1 policy has about 0.3 outcome than the observed policy π.

TABLE 7

| Comparison Policy | Estimated value | Standard Error |
|-------------------|-----------------|----------------|
| s0                | −0.284684       | 0.018630       |
| s1                | 0.300393        | 0.019206       |

The regrets for the optimal policy and the observed policy were computed. Table 8 below includes the comparison results using the training dataset.

TABLE 8

|                   | Regret  | Wrong Decision Ratio |
|-------------------|---------|----------------------|
| $\pi_{DNN}^*(.)$  | 0.00053 | 1.84%                |
| Observed Policy   | 0.28666 | 49.73%               |

Table 9 below includes the comparison results using the testing dataset.

TABLE 9

|                   | Regret  | Wrong Decision Ratio |
|-------------------|---------|----------------------|
| $\pi_{DNN}^*(.)$  | 0.00054 | 1.87%                |
| Observed Policy   | 0.29182 | 50.47%               |

The optimized policy computed by the policy model achieved a significantly lower regret and wrong decision ratio demonstrating the significant value provided using causal inference and policy model application 122 to compute an optimized policy using the policy model instead of the observed policy.

A second experiment was performed in which causal inference and policy model application 122 (CIPM 122) is compared to three other methods: FLM, REG, and REGZ. FLM is a first alternative method introduced in section 7.1 of the *FLM paper*. The *FLM paper* describes regressing t on x, z to estimate $\hat{t}$, $\hat{\zeta}_0(.)$, and $\hat{\zeta}_1(.)$ by the trained treatment model DNN and regressing y on x, z to estimate $\hat{\tilde{\alpha}}(x_i^{(2)})$ and $\hat{\tilde{\beta}}(x_i^{(2)})$ by training the outcome model DNN. The *FLM paper* further describes computing $\hat{\beta}(.)=\hat{\tilde{\beta}}(.)/\hat{\zeta}_1(.)$ and $\hat{\alpha}(.)=\hat{\tilde{\alpha}}(.)-\hat{\beta}(.)\hat{\zeta}_0(.)$. REG is a second alternative method that assumes all confounders are observed and included in the model, uses the influence function method in section 3.1 of the *FLM paper* that regresses p on x, t, z in the treatment model DNN, regresses y on x, t, p in the outcome model DNN, and calculates the influence functions and estimates the parameters of interest as described in the *FLM paper*. REGZ is a third alternative method that assumes all confounders are observed and included in the model, uses the influence function method in section 3.1 of the *FLM paper* that regresses p on x, t, z in the treatment model DNN, regresses y on x, t, z, p in the outcome model DNN, and calculates the influence functions and estimates the parameters of interest as described in the *FLM paper*. For each of the compared four methods, an alternative method (denoted with a (P)) was included that ignored the influence function and instead directly applied $\hat{\alpha}(x^{(2)})$ and $\hat{\beta}(x^{(2)})$ to determine an alpha estimator $$\hat{\theta}_\alpha = \frac{1}{n}\sum_{i=1}^{n} \hat{\alpha}(x_i^{(2)})$$

and a beta estimator $$\hat{\theta}_\beta = \frac{1}{n}\sum_{i=1}^{n} \hat{\beta}(x_i^{(2)}).$$

In the second experiment, the following equations were used to generate data included in input dataset 124.

$$Pr\{s = i\} = \frac{1}{10}, i = 1, \ldots, 10$$

$$\text{time} \sim \text{Uniform}(0, 12)$$

$$\phi_t = 2\left(\frac{50}{3}\left(\frac{\text{time}-6}{12}\right)^4 + \exp\left(-400\left(\frac{\text{time}-6}{12}\right)^2\right) + \frac{\text{time}}{12} - \frac{41}{20}\right)$$

$$t = \zeta_0(\text{time}) + \zeta_1(\text{time})z + v = (5 + 0.3\phi_{time}) + (0.1\phi_{time})z + v$$

$$z, v \sim N(0, 1)$$

$$y = \alpha(s, \text{time}) + \beta(s, \text{time})t + u = (30 + 0.1s\phi_{time}) + (0.1s\phi_{time} - 0.2)t + u$$

$$u \sim N(2v, 1)$$

The treatment variable t is a flight price that is continuous and endogenous. The instrument variable z is a normalized oil price that is continuous. The outcome variable y is a demand that is continuous. The covariates are a customer type and time. The customer type is denoted by s and is discrete. The higher-s customer is more sensitive to the price change. A seasonality is described by $\phi_{time}$ to mimic a seasonality in 12 months. The price t is correlated to the instrument variable z, the normalized oil price. The relationship between the demand y and the price t is described by the constant term $\alpha(.)$ and the slope term $\beta(.)$, where $\beta(.)$ is also called a partial effect. The error term u in equation y is correlated to the error term v in equation t, which indicates that there are unobserved confounders for both the treatment and the outcome. The demand y and the price t are negatively correlated though the partial effect $\beta(x)<0$, $\forall x$ is applied. If y is linearly projected on t, $y=a+bt+\varepsilon$, b is significantly positive. Hence, b is misleading and any decision based on b directly may be wrong.

100 input datasets were generated with 10,000 observations included in each dataset. An estimation of $\alpha(.)$ and $\beta(.)$, an estimation of $\theta_\alpha=E(\alpha(.))$ and $\theta_\beta=E(\beta(.))$, and a policy optimized to maximize the revenue R (t, s, time)=y(t, s, time)*t were computed using each method, where y(t, s, time) is the expected demand given the price t, the customer type s and the time time.

Table 10 below includes a comparison between the statistics computed for each unknown function.

TABLE 10

| | $\alpha(.)$ | | | $\beta(.)$ | | |
|---|---|---|---|---|---|---|
| | Bias | Variance | MSE | Bias | Variance | MSE |
| CIPM 122 | 0.4750 | 4623.5729 | 4624.4011 | −0.1031 | 221.4517 | 221.4911 |
| FLM | 0.3021 | 6053.4397 | 6054.7733 | −0.0689 | 284.2659 | 284.3271 |
| REG | −8.4505 | 24.8698 | 96.2819 | 1.9894 | 1.2855 | 5.2431 |
| REGZ | −8.4835 | 19.4683 | 91.4390 | 1.9987 | 0.9869 | 4.9817 |
| CIPM 122(P) | 0.4081 | 2.2323 | 2.6269 | −0.0761 | 0.1165 | 0.1350 |
| FLM(P) | 0.4683 | 6.2520 | 6.7791 | −0.1003 | 0.2973 | 0.3245 |
| REG(P) | −7.9491 | 0.4637 | 63.6563 | 1.8717 | 0.0090 | 3.5131 |
| REGZ(P) | −8.4773 | 0.5077 | 72.3748 | 2.0052 | 0.0073 | 4.0284 |

The REG and REGZ have a large bias using either estimator. FLM and 2SREG have a large variance resulting in a large MSE. FLM(P) and CIPM 122(P) provide the best results with CIPM 122(P) performing the best.

Table 11 below includes a comparison between the statistics computed for each parameter of interest.

TABLE 11

| | $\theta_\alpha$ | | | $\theta_\beta$ | | |
|---|---|---|---|---|---|---|
| | Bias | Variance | MSE | Bias | Variance | MSE |
| CIPM 122 | 0.4750 | 0.6086 | 0.8343 | −0.1031 | 0.0291 | 0.0397 |
| FLM | 0.3021 | 1.2549 | 1.3462 | −0.0689 | 0.0570 | 0.0618 |
| REG | −8.4505 | 0.0018 | 71.4121 | 1.9894 | 0.0001 | 3.9576 |
| REGZ | −8.4835 | 0.0016 | 71.9707 | 1.9987 | 0.0001 | 3.9948 |
| CIPM 122(P) | 0.4081 | 0.2303 | 0.3968 | −0.0761 | 0.0129 | 0.0186 |
| FLM(P) | 0.4683 | 0.3109 | 0.5302 | −0.1003 | 0.0173 | 0.0273 |
| REG(P) | −7.9491 | 0.0040 | 63.1927 | 1.8717 | 0.0006 | 3.5041 |
| REGZ(P) | −8.4773 | 0.0028 | 71.8672 | 2.0052 | 0.0004 | 4.0211 |

Due to the very large bias, REG and REGZ are not good estimators using either estimator due to the erroneous assumption that all confounders are observed and included in the model. In fact, the estimations of $\theta_\beta$ using REG and REGZ are significantly positive, which is wrong.

Based on the results, the plug-in version CIPM 122(P) and FLM(P) resulted in a smaller MSE. However, Table 12 shows the coverage rate in the 100 simulations for a 95% confidence interval estimated by each method, where the closer the coverage is to 95%, the better the method performed. CIPM 122(P) and FLM(P) provide a very small coverage, which is one of the main reasons why plug-in estimators are not good estimators for parameters of interest.

TABLE 12

|  | CIPM 122 | FLM | REG | REGZ | FLM(P) | CIPM 122(P) | REG(P) | REGZ(P) |
|---|---|---|---|---|---|---|---|---|
| $\theta_\alpha$ | 0.95 | 0.96 | 0.00 | 0.00 | 0.03 | 0.05 | 0.00 | 0.00 |
| $\theta_\beta$ | 0.94 | 0.95 | 0.00 | 0.00 | 0.15 | 0.14 | 0.00 | 0.00 |

CIPM 122 and FLM both provide good coverage and are good estimators of parameters of interest. CIPM 122 is an improvement over FLM because it resulted in a smaller MSE.

The optimized policy depends on the accuracy of estimation of $\alpha(.)$ and $\beta(.)$. Since CIPM 122(P) provided the best estimators of $\alpha(.)$ and $\beta(.)$, a difference between each method's optimized revenue and that computed using CIPM 122(P) is shown in Table 13.

TABLE 13

|  | Mean | Standard Deviation | t-Statistic | p-value |
|---|---|---|---|---|
| CIPM 122 | −87.1000 | 13.9123 | −62.6063 | <.0001 |
| FLM | −86.7999 | 14.5709 | −59.5708 | <.0001 |
| REG | −129.2880 | 14.6301 | −88.3711 | <.0001 |
| REGZ | −130.8220 | 14.6651 | −89.2061 | <.0001 |
| FLM(P) | −8.0084 | 16.7019 | −4.7949 | <.0001 |
| REG(P) | −139.5010 | 14.6128 | −95.4649 | <.0001 |
| REGZ(P) | −140.7020 | 14.6580 | −95.9897 | <.0001 |

The differences are all significantly negative, which means that CIPM 122(P) is the best method for policy optimization in this experiment. In fact, over the 100 simulations, CIPM 122(P) achieved an average optimized revenue of 163.5121, which is about 80% of the true optimized revenue 206.0194.

Figure 4:
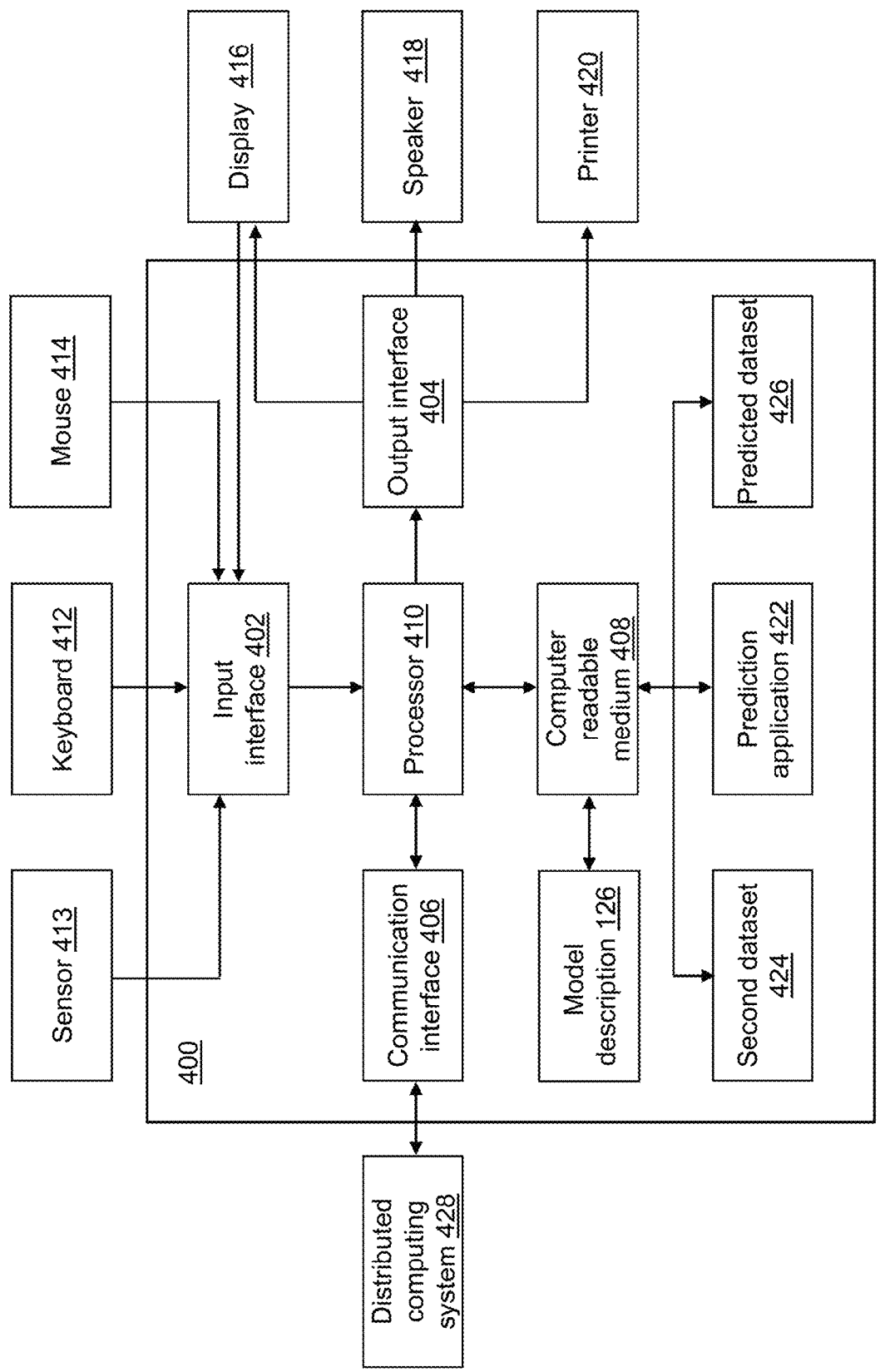
FIG. 4 depicts a block diagram of a prediction device in accordance with an illustrative embodiment.

Referring to FIG. 4, a block diagram of a prediction device 400 is shown in accordance with an illustrative embodiment. Prediction device 400 may include a second input interface 402, a second output interface 404, a second communication interface 406, a second non-transitory computer-readable medium 408, a second processor 410, a prediction application 422, model description 126, second dataset 424, and predicted dataset 426. Fewer, different, and/or additional components may be incorporated into prediction device 400. Prediction device 400 and model training device 100 may be the same or different devices.

Second input interface 402 provides the same or similar functionality as that described with reference to input interface 102 of model training device 100 though referring to prediction device 400. Second output interface 404 provides the same or similar functionality as that described with reference to output interface 104 of model training device 100 though referring to prediction device 400. Second communication interface 406 provides the same or similar functionality as that described with reference to communication interface 106 of model training device 100 though referring to prediction device 400. Data and messages may be transferred between prediction device 400 and a distributed computing system 428 using second communication interface 406. Distributed computing system 130 and distributed computing system 428 may be the same or different computing systems. Second computer-readable medium 408 provides the same or similar functionality as that described with reference to computer-readable medium 108 of model training device 100 though referring to prediction device 400. Second processor 410 provides the same or similar functionality as that described with reference to processor 110 of model training device 100 though referring to prediction device 400.

Prediction application 422 performs operations associated with predicting a treatment value for each observation vector included in second dataset 424. The predicted treatment value may be stored in predicted dataset 426 to support various data analysis functions as well as provide alert/messaging related to each predicted treatment value. Some or all of the operations described herein may be embodied in prediction application 422. The operations may be implemented using hardware, firmware, software, or any combination of these methods.

Referring to the example embodiment of FIG. 4, prediction application 422 is implemented in software (comprised of computer-readable and/or computer-executable instructions) stored in second computer-readable medium 408 and accessible by second processor 410 for execution of the instructions that embody the operations of prediction application 422. Prediction application 422 may be written using one or more programming languages, assembly languages, scripting languages, etc. Prediction application 422 may be integrated with other analytic tools. As an example, prediction application 422 may be part of an integrated data analytics software application and/or software architecture such as that offered by SAS Institute Inc. of Cary, N.C., USA. For example, prediction application 422 may be part of SAS® Enterprise Miner™ developed and provided by SAS Institute Inc. of Cary, N.C., USA. Merely for further illustration, prediction application 422 may be implemented using or integrated with one or more SAS software tools such as Base SAS, SAS/STAT®, SAS® High Performance Analytics Server, SAS® LASR™, SAS® In-Database Products, SAS® Scalable Performance Data Engine, SAS/OR®, SAS/ETS®, SAS® Econometrics, SAS® Visual Analytics, SAS® Viya™, and SAS In-Memory Statistics for Hadoop®, all of which are developed and provided by SAS Institute Inc. of Cary, N.C., USA.

One or more operations of prediction application 422 further may be performed by an ESPE on an event stream instead of reading observation vectors from second dataset 424. Prediction application 422 and causal inference and policy model application 122 may be the same or different applications that are integrated in various manners to train the policy model using input dataset 124 that may be distributed on distributed computing system 130 and to execute the trained policy model to predict the treatment value for each observation vector included in second dataset 424 that may be distributed on distributed computing system 428.

Prediction application 422 may be implemented as a Web application. Prediction application 422 may be integrated with other system processing tools to automatically process data generated as part of operation of an enterprise, to predict a treatment value, and/or to provide a warning or alert associated with the prediction using second input interface 402, second output interface 404, and/or second communication interface 406 so that appropriate action can be initiated in response. For example, a warning or an alert may be presented using a second display 416, a second speaker 418, a second printer 420, etc. or sent to one or more computer-readable media, display, speaker, printer, etc. of distributed computing system 428.

Input dataset 124 and second dataset 424 may be generated, stored, and accessed using the same or different mechanisms. The treatment variable and the outcome variable are not defined in second dataset 424. Similar to input dataset 124, second dataset 424 may include a plurality of rows and a plurality of columns with the plurality of rows referred to as observations or records, and the columns referred to as variables that are associated with an observation. Second dataset 424 may be transposed.

Similar to input dataset 124, second dataset 424 may be stored on second computer-readable medium 408 or on one or more computer-readable media of distributed computing system 428 and accessed by prediction device 400 using second communication interface 406. Data stored in second dataset 424 may be a sensor measurement or a data communication value, for example, from a sensor 513, may be generated or captured in response to occurrence of an event or a transaction, generated by a device such as in response to an interaction by a user with the device, for example, from a second keyboard 412 or a second mouse 414, etc. The data stored in second dataset 424 may include any type of content represented in any computer-readable format such as binary, alphanumeric, numeric, string, markup language, etc. The content may include textual information, graphical information, image information, audio information, numeric information, etc. that further may be encoded using various encoding techniques as understood by a person of skill in the art. The data stored in second dataset 424 may be captured at different time points periodically, intermittently, when an event occurs, etc. One or more columns may include a time value. Similar to input dataset 124, data stored in second dataset 424 may be generated as part of the IoT, and some or all data may be pre- or post-processed by an ESPE.

Similar to input dataset 124, second dataset 424 may be stored in various compressed formats such as a coordinate format, a compressed sparse column format, a compressed sparse row format, etc. Second dataset 424 further may be stored using various structures as known to those skilled in the art including a file system, a relational database, a system of tables, a structured query language database, etc. on prediction device 400 and/or on distributed computing system 428. Prediction device 400 may coordinate access to second dataset 424 that is distributed across a plurality of computing devices that make up distributed computing system 428. For example, second dataset 424 may be stored in a cube distributed across a grid of computers as understood by a person of skill in the art. As another example, second dataset 424 may be stored in a multi-node Hadoop® cluster. As another example, second dataset 424 may be stored in a cloud of computers and accessed using cloud computing technologies, as understood by a person of skill in the art. The SAS® LASR™ Analytic Server and/or SAS® Viya™ may be used as an analytic platform to enable multiple users to concurrently access data stored in second dataset 424.

Figure 5:
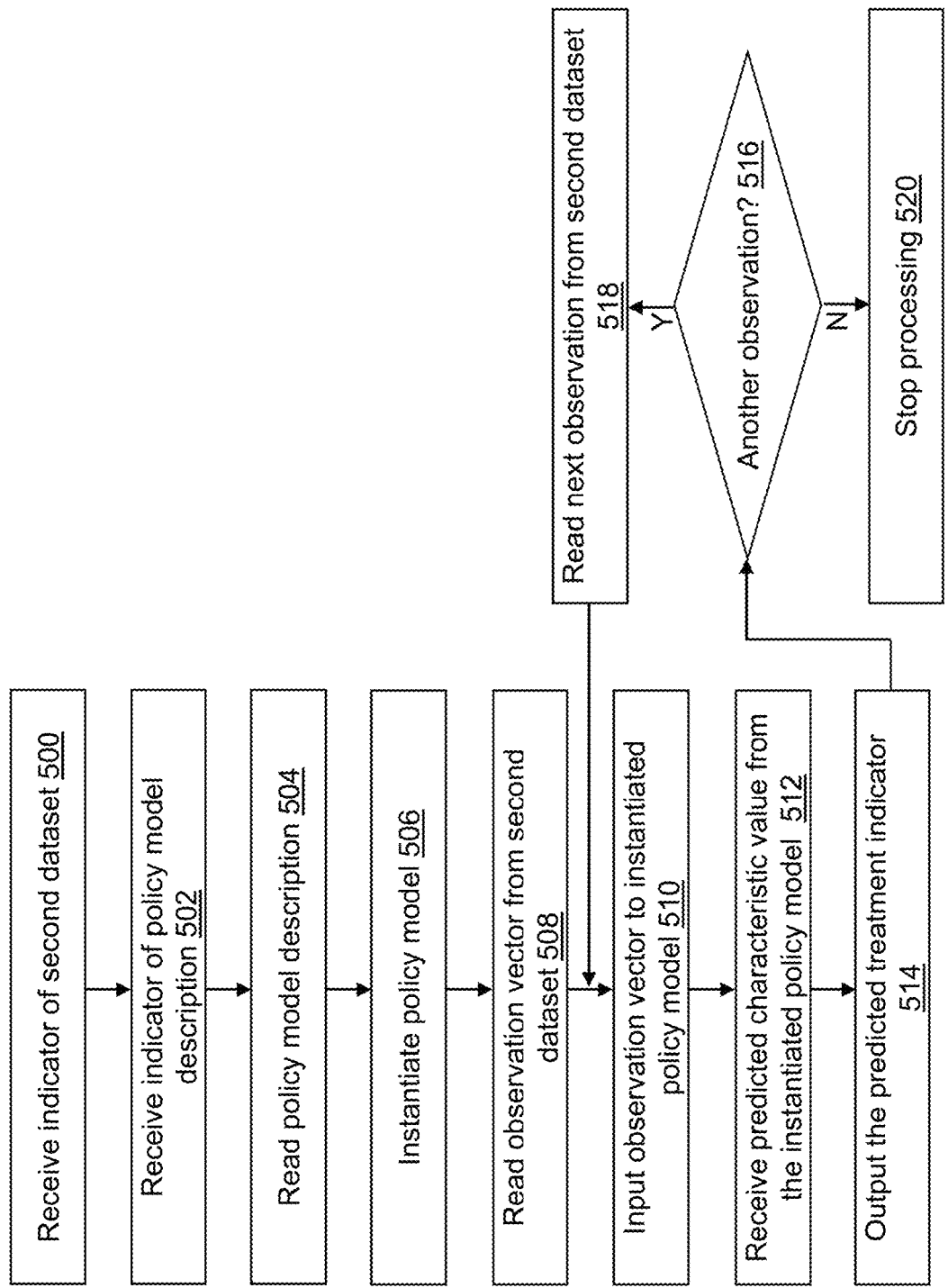
FIG. 5 depicts a flow diagram illustrating examples of operations performed by the prediction device of FIG. 4 in accordance with an illustrative embodiment.

Referring to FIG. 5, example operations of prediction application 422 are described. Additional, fewer, or different operations may be performed depending on the embodiment of prediction application 422. The order of presentation of the operations of FIG. 5 is not intended to be limiting. Although some of the operational flows are presented in sequence, the various operations may be performed in various repetitions, concurrently (in parallel, for example, using threads and/or distributed computing system 428), and/or in other orders than those that are illustrated.

In an operation 500, an eighth indicator may be received that indicates second dataset 424. For example, the eighth indicator indicates a location and a name of second dataset 424. As an example, the eighth indicator may be received by prediction application 422 after selection from a user interface window or after entry by a user into a user interface window. In an alternative embodiment, second dataset 424 may not be selectable. For example, a most recently created dataset may be used automatically.

In an operation 502, a ninth indicator may be received that indicates model description 126. For example, the ninth indicator indicates a location and a name of model description 126. As an example, the ninth indicator may be received by prediction application 422 after selection from a user interface window or after entry by a user into a user interface window. In an alternative embodiment, model description 126 may not be selectable. For example, a most recently created model configuration data may be used automatically. As another example, model description 126 may be provided automatically as part of integration with causal inference and policy model application 122.

In an operation 504, a policy model description is read from model description 126.

In an operation 506, a policy model is instantiated with the policy model description. For example, the architecture of the policy model, its hyperparameters, its weight vector, and other characterizing elements are read and used to instantiate a DNN based on the information output from the training process in operation 260.

In an operation 508, an observation vector is read from second dataset 424.

In an operation 510, the observation vector is input to the instantiated model.

In an operation 512, a predicted treatment value for the read observation vector is received as an output of the instantiated model.

In an operation 514, the predicted treatment value may be output, for example, by storing the predicted treatment value with the observation vector to predicted dataset 426. In addition, or in the alternative, the predicted treatment value may be presented on second display 416, printed on second printer 420, sent to another computing device using second communication interface 406, an alarm or other alert signal may be sounded through second speaker 418, etc.

In an operation 516, a determination is made concerning whether or not second dataset 424 includes another observation vector. When second dataset 424 includes another observation vector, processing continues in an operation 518. When second dataset 424 does not include another observation vector, processing continues in an operation 520.

In operation 518, a next observation vector is read from second dataset 424, and processing continues in operation 510.

In operation 520, processing stops and cleanup is performed as needed.

There are applications for causal inference and policy model application 122 and prediction application 422 in many areas such as stratification in clinical trials, customer targeting, personalized pricing, click-through-rate learning, etc. The presented results demonstrate that the trained policy model is very close to a theoretical optimum policy. The explosion of digital data is generating many opportunities for big data analytics, which in turn provides many opportunities for training neural network models to capitalize on the information contained in the data—to make better predictions that lead to better decisions.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, using "and" or "or" in the detailed description is intended to include "and/or" unless specifically indicated otherwise. The illustrative embodiments may be implemented as a method, apparatus, or article of manufacture using standard programming and/or engineering techniques to produce software, firmware, hardware, or any combination thereof to control a computer to implement the disclosed embodiments.

The foregoing description of illustrative embodiments of the disclosed subject matter has been presented for purposes of illustration and of description. It is not intended to be exhaustive or to limit the disclosed subject matter to the precise form disclosed, and modifications and variations are possible in light of the above teachings or may be acquired from practice of the disclosed subject matter. The embodiments were chosen and described in order to explain the principles of the disclosed subject matter and as practical applications of the disclosed subject matter to enable one skilled in the art to utilize the disclosed subject matter in various embodiments and with various modifications as suited to the particular use contemplated.

What is claimed is:

1. A non-transitory computer-readable medium having stored thereon computer-readable instructions that when executed by a computing device cause the computing device to:
   train a treatment model to optimize a treatment loss function based on a treatment variable t using a plurality of observation vectors, wherein covariate variable values for a plurality of covariate variables, a treatment variable value for the treatment variable t, an instrument variable value for an instrument variable z, and an outcome variable value for an outcome variable y are defined for each observation vector of the plurality of observation vectors, wherein the treatment model is a first neural network that includes a first plurality of connected neural network layers, wherein the treatment model is trained to regress t on $x_i^{(1)}$, z, wherein $x_i^{(1)}$ indicates a first set of covariate variable values defined for a first set of covariate variables $x^{(1)}$ selected from the plurality of covariate variables, where i indicates an $i^{th}$ observation vector of the plurality of observation vectors;
   execute the trained treatment model to compute an estimated treatment variable value $\hat{t}_i$ for each observation vector of the plurality of observation vectors;
   train an outcome model to optimize an outcome loss function, wherein the outcome model is a second neural network that includes a second plurality of connected neural network layers, wherein the outcome model is trained to regress y on $x^{(2)}$ and an estimated treatment variable $\hat{t}$, wherein $x_i^{(2)}$ indicates a second set of covariate variable values defined for a second set of covariate variables $x^{(2)}$ selected from the plurality of covariate variables;
   execute the trained outcome model to compute an estimated first unknown function value $\hat{\alpha}(x_i^{(2)})$ and an estimated second unknown function value $\hat{\beta}(x_i^{(2)})$ for each observation vector of the plurality of observation vectors;
   compute an influence function value for a predefined parameter of interest using the estimated first unknown function value $\hat{\alpha}(x_i^{(2)})$ and the estimated second unknown function value $\hat{\beta}(x_i^{(2)})$ for each observation vector of the plurality of observation vectors;
   compute a value for the predefined parameter of interest using the computed influence function value; and
   output the computed value for the predefined parameter of interest.

2. The non-transitory computer-readable medium of claim 1, wherein the first set of covariate variables and the second set of covariate variables are identical.

3. The non-transitory computer-readable medium of claim 1, wherein the trained treatment model is further executed to compute an estimated third unknown function value $\hat{p}(x_i^{(1)})$ for each observation vector of the plurality of observation vectors.

4. The non-transitory computer-readable medium of claim 3, wherein the influence function value for the predefined parameter of interest is further computed using the estimated third unknown function value $\hat{p}(x_i^{(1)})$ for each observation vector of the plurality of observation vectors.

5. The non-transitory computer-readable medium of claim 1, wherein the influence function value for the predefined parameter of interest is computed directly from the estimated first unknown function value $\hat{\alpha}(x_i^{(2)})$ and the estimated second unknown function value $\hat{\beta}(x_i^{(2)})$ for each observation vector of the plurality of observation vectors.

6. The non-transitory computer-readable medium of claim 1, wherein the influence function value for the predefined parameter of interest is computed by training a plurality of neural networks to estimate a matrix function using $\Lambda(.) = (\lambda_{ij}(.))_{i,j=1,\ldots,1+K}$, where $\Lambda(.)$ is the matrix function, the plurality of neural networks include $N=K(K+1)/2$ neural networks, K is a dimension of the treatment variable t, $\lambda_{ij}(.) = \dot{G}(\hat{\alpha}(x^{(2)}) + \hat{\beta}(x^{(2)})'t)t_{i-1}, t_{j-1}$, $t_{i-1}$ is an $(i-1)^{th}$ element of the treatment variable t, $t_{j-1}$ is a $(j-1)^{th}$ element of the treatment variable t, and $\dot{G}$ is a predefined derivative of $\hat{\alpha}(x^{(2)}) + \hat{\beta}(x^{(2)})'t$, and ' indicates a transpose.

7. The non-transitory computer-readable medium of claim 1, wherein the trained treatment model is further executed to compute an estimated outcome variable value $\hat{y}_i$ for each observation vector of the plurality of observation vectors.

8. The non-transitory computer-readable medium of claim 7, wherein the estimated outcome variable value $\hat{y}_i$ for each observation vector of the plurality of observation vectors is computed using $\hat{y}_i = \hat{\alpha}(x_i^{(2)}) + \hat{\beta}(x_i^{(2)})'\hat{t}_i$, where $\hat{\alpha}(x_i^{(2)})$ is an $i^{th}$ value of the estimated first unknown function, and $\hat{\beta}(x_i^{(2)})$ is an $i^{th}$ value of the estimated second unknown function.

9. The non-transitory computer-readable medium of claim 1, wherein the value for the predefined parameter of interest is computed as a mean of the influence function value computed for each observation vector of the plurality of observation vectors.

10. The non-transitory computer-readable medium of claim 9, wherein a standard error of the value for the predefined parameter of interest is further computed as a quotient of a standard error of the influence function value computed for each observation vector of the plurality of observation vectors and a square root of a number of observations vectors included in the plurality of observation vectors.

11. The non-transitory computer-readable medium of claim 1, wherein the computer-readable instructions further cause the computing device to:
   read an observation vector from a dataset;
   instantiate a prediction model from the trained treatment model;
   compute a predicted treatment for the read observation vector using the instantiated prediction model; and
   output the computed predicted treatment for the read observation vector.

12. The non-transitory computer-readable medium of claim 1, wherein the computer-readable instructions further cause the computing device to:
   read an observation vector from a dataset;
   instantiate a prediction model from the trained outcome model;
   compute a predicted outcome for the read observation vector using the instantiated prediction model; and
   output the computed predicted outcome for the read observation vector.

13. The non-transitory computer-readable medium of claim 1, wherein the trained treatment model is further executed to compute an estimated third unknown function value $\hat{\zeta}_0(x_i^{(1)})$ and an estimated fourth unknown function value $\hat{\zeta}_1(x_i^{(1)})$ for each observation vector of the plurality of observation vectors.

14. The non-transitory computer-readable medium of claim 13, wherein the influence function value for the predefined parameter of interest is computed using $\hat{\hat{\alpha}}(x_i^{(2)})$ and $\hat{\hat{\beta}}(x_i^{(2)})$, where $\hat{\hat{\alpha}}(x_i^{(2)})=\hat{\alpha}(x_i^{(2)})+\hat{\beta}(x_i^{(2)})\hat{\zeta}_0(x_i^{(2)})$, and $\hat{\hat{\beta}}(x_i^{(2)})=\hat{\beta}(x_i^{(2)})\hat{\zeta}_1(x_i^{(2)})$ and $x_i^{(2)}=x_i^{(1)}$.

15. The non-transitory computer-readable medium of claim 1, wherein, after executing the trained outcome model, the computer-readable instructions further cause the computing device to:
   train a policy model to optimize a predefined value function, wherein the policy model is a third neural network that includes a third plurality of connected neural network layers, wherein the policy model is trained to maximize the predefined value function on $x_i^{(3)}$, $\hat{\alpha}(x_i^{(3)})$, and $\hat{\beta}(x_i^{(3)})$, wherein $x^{(3)}$ indicates a third set of covariate variable values defined for a third set of covariate variables $x_i^{(3)}$ selected from the plurality of covariate variables; and
   store the trained policy model.

16. The non-transitory computer-readable medium of claim 15, wherein the computer-readable instructions further cause the computing device to:
   read an observation vector from a dataset;
   instantiate a prediction model from the trained policy model;
   compute a predicted policy for the read observation vector using the instantiated prediction model; and
   output the computed predicted policy of the read observation vector.

17. The non-transitory computer-readable medium of claim 15, wherein the first set of covariate variables, the second set of covariate variables, and the third set of covariate variables are identical.

18. The non-transitory computer-readable medium of claim 15, wherein the first set of covariate variables and the third set of covariate variables are identical.

19. The non-transitory computer-readable medium of claim 15, wherein the second set of covariate variables and the third set of covariate variables are identical.

20. The non-transitory computer-readable medium of claim 15, wherein the computer-readable instructions further cause the computing device to select a predefined number of most important variables from the first set of covariate variables, wherein the third set of covariate variables are the predefined number of most important variables selected from the first set of covariate variables.

21. The non-transitory computer-readable medium of claim 20, wherein the computer-readable instructions further cause the computing device to select a predefined number of most important variables from the second set of covariate variables, wherein the third set of covariate variables further include the predefined number of most important variables selected from the second set of covariate variables.

22. The non-transitory computer-readable medium of claim 15, wherein the computer-readable instructions further cause the computing device to select a predefined number of most important variables from the second set of covariate variables, wherein the third set of covariate variables are the predefined number of most important variables selected from the second set of covariate variables.

23. The non-transitory computer-readable medium of claim 15, wherein the predefined value function is a negative value function.

24. The non-transitory computer-readable medium of claim 23, wherein the influence function value for the predefined parameter of interest is computed directly from the estimated first unknown function value $\hat{\alpha}(x_i^{(2)})$ and the estimated second unknown function value $\hat{\beta}(x_i^{(2)})$ for each observation vector of the plurality of observation vectors.

25. The non-transitory computer-readable medium of claim 23, wherein the influence function value for the predefined parameter of interest is computed by training a plurality of neural networks to estimate a matrix function using $\Lambda(.)=(\lambda_{ij}(.))_{i,j=1, \ldots, 1+K}$, where $\Lambda(.)$ is the matrix function, the plurality of neural networks include $N=K(K+1)/2$ neural networks, K is a dimension of the treatment variable t, $\lambda_{ij}(.)=\dot{G}(\hat{\alpha}(x^{(2)})+\hat{\beta}(x^{(2)})'t)t_{i-1}, t_{j-1}, t_{i-1}$ is an $(i-1)^{th}$ element of the treatment variable t, $t_{j-1}$ is a $(j-1)^{th}$ element of the treatment variable t, and $\dot{G}$ is a predefined derivative of $\hat{\alpha}(x^{(2)})+\hat{\beta}(x^{(2)})'t$, and ' indicates a transpose.

26. The non-transitory computer-readable medium of claim 1, wherein the computer-readable instructions further cause the computing device to:
   read an observation vector from a dataset;
   compute a predicted policy for the read observation vector using $\hat{\beta}(x_i^{(2)})>0$; and
   output the computed predicted policy of the read observation vector.

27. The non-transitory computer-readable medium of claim 1, wherein the computer-readable instructions further cause the computing device to:
   read an observation vector from a dataset;
   execute the trained treatment model to determine a treatment value for the read observation vector;
   compute a predicted policy for the read observation vector using $\hat{\beta}(x_i^{(2)})>c/m$, where c is a predefined cost defined for the determined treatment value, and m is a predefined profit margin; and
   output the computed predicted policy of the read observation vector.

28. The non-transitory computer-readable medium of claim 1, wherein the computer-readable instructions further cause the computing device to:

read an observation vector from a dataset;
compute a predicted policy for the read observation vector using $$-\frac{1}{2}\frac{\hat{\alpha}(x_i^{(2)})}{\hat{\beta}(x_i^{(2)})};$$

and
output the computed predicted policy of the read observation vector.

29. A computing device comprising:
a processor; and
a computer-readable medium operably coupled to the processor, the computer-readable medium having computer-readable instructions stored thereon that, when executed by the processor, cause the computing device to
train a treatment model to optimize a treatment loss function based on a treatment variable t using a plurality of observation vectors, wherein covariate variable values for a plurality of covariate variables, a treatment variable value for the treatment variable t, an instrument variable value for an instrument variable z, and an outcome variable value for an outcome variable y are defined for each observation vector of the plurality of observation vectors, wherein the treatment model is a first neural network that includes a first plurality of connected neural network layers, wherein the treatment model is trained to regress t on $x(x_i^{(2)})$, z, wherein $x_i^{(1)}$ indicates a first set of covariate variable values defined for a first set of covariate variables $x^{(1)}$ selected from the plurality of covariate variables, where i indicates an $i^{th}$ observation vector of the plurality of observation vectors;
execute the trained treatment model to compute an estimated treatment variable value $\hat{t}_i$ for each observation vector of the plurality of observation vectors;
train an outcome model to optimize an outcome loss function, wherein the outcome model is a second neural network that includes a second plurality of connected neural network layers, wherein the outcome model is trained to regress y on $x^{(2)}$ and an estimated treatment variable $\hat{t}$, wherein $x_i^{(2)}$ indicates a second set of covariate variable values defined for a second set of covariate variables $x^{(2)}$ selected from the plurality of covariate variables;
execute the trained outcome model to compute an estimated first unknown function value $\hat{\alpha}(x_i^{(2)})$ and an estimated second unknown function value $\hat{\beta}(x_i^{(2)})$ for each observation vector of the plurality of observation vectors;
compute an influence function value for a predefined parameter of interest using the estimated first unknown function value $\hat{\alpha}(x_i^{(2)})$ and the estimated second unknown function value $\hat{\beta}(x_i^{(2)})$ for each observation vector of the plurality of observation vectors;
compute a value for the predefined parameter of interest using the computed influence function value; and
output the computed value for the predefined parameter of interest.

30. A method of training neural network models to estimate a value for a parameter of interest for causal inference, the method comprising:
training, by a computing device, a treatment model to optimize a treatment loss function based on a treatment variable t using a plurality of observation vectors, wherein covariate variable values for a plurality of covariate variables, a treatment variable value for the treatment variable t, an instrument variable value for an instrument variable z, and an outcome variable value for an outcome variable y are defined for each observation vector of the plurality of observation vectors, wherein the treatment model is a first neural network that includes a first plurality of connected neural network layers, wherein the treatment model is trained to regress t on $x(x_i^{(2)})$, z, wherein $x_i^{(1)}$ indicates a first set of covariate variable values defined for a first set of covariate variables $x^{(1)}$ selected from the plurality of covariate variables, where i indicates an $i^{th}$ observation vector of the plurality of observation vectors;
executing, by the computing device, the trained treatment model to compute an estimated treatment variable value $\hat{t}_i$ for each observation vector of the plurality of observation vectors;
training, by the computing device, an outcome model to optimize an outcome loss function, wherein the outcome model is a second neural network that includes a second plurality of connected neural network layers, wherein the outcome model is trained to regress y on $x^{(2)}$ and an estimated treatment variable $\hat{t}$, wherein $x_i^{(2)}$ indicates a second set of covariate variable values defined for a second set of covariate variables $x^{(2)}$ selected from the plurality of covariate variables;
executing, by the computing device, the trained outcome model to compute an estimated first unknown function value $\hat{\alpha}(x_i^{(2)})$ and an estimated second unknown function value $\hat{\beta}(x_i^{(2)})$ for each observation vector of the plurality of observation vectors;
computing, by the computing device, an influence function value for a predefined parameter of interest using the estimated first unknown function value $\hat{\alpha}(x_i^{(2)})$ and the estimated second unknown function value $\hat{\beta}(x_i^{(2)})$ for each observation vector of the plurality of observation vectors;
computing, by the computing device, a value for the predefined parameter of interest using the computed influence function value; and
outputting, by the computing device, the computed value for the predefined parameter of interest.

* * * * *

UNITED STATES PATENT AND TRADEMARK OFFICE
CERTIFICATE OF CORRECTION

PATENT NO. : 11,354,566 B1
APPLICATION NO. : 17/507376
DATED : June 7, 2022
INVENTOR(S) : Xilong Chen et al.

It is certified that error appears in the above-identified patent and that said Letters Patent is hereby corrected as shown below:

In the Specification

Column 14, Line 47:
Delete the phrase "$t$ ort" and replace with --$t$ or $\hat{t}$--.

Column 15, Lines 18-19:
Delete the phrase "an a parameter layer 306 and to a parameter layer 308." and replace with --an $\alpha$ parameter layer 306 and to a $\beta$ parameter layer 308.--.

In the Claims

Claim 29, Column 33, Line 32:
Delete the phrase "$x(x_i^{(2)})$, $z$, wherein $x_i^{(1)}$ )" replace with --$x^{(1)}$, $z$, wherein $x_i^{(1)}$ --.

Claim 30, Column 34, Line 23:
Delete the phrase "$x(x_i^{(2)})$, $z$, wherein $x_i^{(1)}$" replace with --$x^{(1)}$, $z$, wherein $x_i^{(1)}$ --.

Signed and Sealed this
First Day of November, 2022

*Katherine Kelly Vidal*

Katherine Kelly Vidal
*Director of the United States Patent and Trademark Office*